United States Patent [19]
Hubbell et al.

[11] Patent Number: 5,278,063
[45] Date of Patent: Jan. 11, 1994

[54] CHEMICAL MODIFICATION OF PROMOTE ANIMAL CELL ADHESION ON SURFACES

[75] Inventors: Jeffrey A. Hubbell; Stephen P. Massia, both of Austin, Tex.

[73] Assignee: Board of Regents The University of Texas System, Austin, Tex.

[21] Appl. No.: 414,144

[22] Filed: Sep. 28, 1989

[51] Int. Cl.$^5$ .......................... C12N 5/00; C07K 5/10; C07K 7/06
[52] U.S. Cl. .......................... 435/240.243; 435/240.23; 530/329; 530/330
[58] Field of Search .. 435/240.23, 435/240, 435/243; 530/329, 330

[56] References Cited

U.S. PATENT DOCUMENTS 4,614,517  9/1986  Ruoslahti et al. .................. 530/330
5,092,885  3/1992  Yamada et al. ........................ 623/11

FOREIGN PATENT DOCUMENTS 0278781  8/1988  European Pat. Off. .
88/01279  2/1988  World Int. Prop. O. .

OTHER PUBLICATIONS

Graf, et al. A Pentapeptide from the Laminin B1 Chain Mediates Cell Adhesion and Binds the 67,000 Laminin Receptor Biochemistry vol. 26 No. 22 pp. 6896-6900 1987.
Humphries, et al. Identification of an Alternatively Spliced Site in Human Plasma Fibronectin that Mediates Cell . . . Journal of Cell Biology vol. 103 No. 6 Pt. 2 pp. 2637-2647 1986.
Brandley et al. Covalent Attachment of an Arg--Gly-Asp Sequence Peptide to Derivatizable Polyacrylamide Surfaces . . . Analytical Biochemistry vol. 172 pp. 270-278 1988.
Nilsson, et al. Immobilization of Enzymes and Affinity Ligands to Various Hydroxyl Group Carrying Supports . . . Biochem Biophys Research Comm. vol. 102 No. 1 pp. 449-457 1981.
Raja, et al., Preparation and Use of Synthetic Cell Culture Surfaces J. Biological Chemistry vol. 261, pp. 8505-8513 1986.
Underwood et al., (1989) J. Cell Sci. 93:641-649.
Brandley et al., (1989) Dev. Viol. 135:74-86.
Danilov et al. (1989) Exp. Cel. Res. 182:186-196.
International Search Report (1991).
Idemitsu Kosan K.K. (1988) WPI Acc. No. 88-35 1050/49 JP A, 63264069.
Yamada et al (1989) WPI Acc. No. 89-1505g/20 and U.S., A, Jul. 22, 1982.
Tashiro et al. (1989) J. Biol. Chem. 264(27); 16174-82.
Gregonis et al (1978), Polymer 19:1279-1284.
Cheresh, A., (1987), Proc. Natl. Acad. Sci., USA 84:6471-6475.
Ohlson, et al., (1978), FEBS Letters, 93, 5-9.
Woods, et al., (1986), EMBO J., 5: 665-670.
Streeter, et al., (1987), J. Cell. Biol., 105: 507-515.
Paul, et al., (1976), J. Appl. Pol. Sci., 20: 609-625.
Mohr & Pommerening, (1985), Affinity Chromatography: practical and theoretical aspects, Chapter 4.
Costello & McCarthy, (1987), Macromolecules, 20: 2819-2828.

(List continued on next page.)

*Primary Examiner*—George C. Elliott
*Attorney, Agent, or Firm*—Arnold, White & Durkee

[57] ABSTRACT

A cell culture substrate which promotes cell adhesion and the formation of focal contacts is disclosed. Polymer, ceramic and glass surfaces may be used. The surfaces are derivatized with peptides having less than 12 amino acid residues and containing one of the following sequences of amino acids: GRGD, GYIGSR, GREDV. The peptides are covalently attached to the surface through the terminal amino group of the N-terminal glycine residue, and are effective at concentrations of about 50 picomoles or less per cm$^2$ of surface area. Methods of preparing the surfaces are disclosed.

25 Claims, 13 Drawing Sheets

OTHER PUBLICATIONS

Hynes, et al., (1982), J. Cell. Biol., 95: 369–377.
Pierschbacher, et al., (1984), Nature, 309: 30–33.
Pytela, et al., (1985), Cell, 40: 191–198.
Pytela, et al., (1985), Proc. Natl. Acad. Sci., USA, 82: 5766–5770.
Fitzgerald, et al., (1985), J. Biol. Chem., 260: 11366–11374.
Ruoslahti, et al., (1987), Science, 238: 491–497.
Hynes, R. O., (1987), Cell, 48: 549–554.
Grinnell, F., (1978), "Cellular Adhesiveness and Extracellular Substrata", International Review of Cytology, 53: 67–149.
Couchman, et al., (1982), J. Cell Biol., 93: 402–410.
Pearlstein, E., (1976), Nature, 262: 497–500.
Kleinman, et al., (1976), Biochem. Biophys. Res. Commun., 72: (2) 426–432.
Grinnell, F., (1976), Exp. Cell Res., 97: 265–274.
Grinnell, F., (1976), Exp. Cell Res., 102: 51–62.
Singer, et al., (1987), J. Cell. Biol., 104: 573–584.
Variani, et al., (1986), In Vivo, 22: 575–582.
Aubert, et al., (1987), J. Biomed. Mater Res., 21: 585–602.
Mugnai, et al., (1988), J. Cell Biol., 106: 931.
Singer, et al., (1988), J. Cell Biol., 106: 2171.
Dejana, et al., J. Cell Biol., 104: 1403, (1987) (Abstract).
Lark et al. (1985) *Federation Proceedings*, 44:394–403.
Izzard et al. (1986) *Experimental Cell Research*, 165:320–336.

CHEMICAL MODIFICATION OF PROMOTE ANIMAL CELL ADHESION ON SURFACES

The U.S. Government may have rights in the present invention as relevant developmental work was supported by National Science Foundation Grant CBT-881020268, and National Institutes of Health Grant HL-39714.

Reference is specifically made herein the copending application, U.S. Ser. No. 07/527,198, filed May 21, 1990.

BACKGROUND OF THE INVENTION

1. Field of the Invention

The field of the present invention relates generally to the biospecific adhesion of cells to a surface. More specifically, the invention relates to the chemical modification of a surface and the covalent attachment thereto of small peptides to promote cell adhesion. Even more particularly, the surface may comprise a ceramic, a metal or a polymer. The small peptides include a minimal cell receptor recognition amino acid sequence which promotes cell adhesion and is common to a variety of cell adhesion molecules. The surfaces and methods of the present invention thus relate to cell adhesion techniques which are independent of culture media serum composition and adsorbed surface proteins.

2. Description of the Related Art

The interaction of cells with extracellular matrix in vivo is involved in a number of important biological processes, such as the regulation of cellular growth, migration, and differentiation. The role of eukaryotic cell adhesion in culture largely dictates the success of a particular cell culture effort or endeavor. Adhesion, spreading, and contraction on solid substances are prerequisites for growth of normal anchorage dependent cells in vitro (1, 2). This cellular bioadhesion is affected by several factors, including the particular type of cell, the cell culture media used, and the particular surface upon which the cells are cultured.

Many mammalian cells are cultured on polymer surfaces. Nearly all mammalian cell adhesion to synthetic polymer surfaces is controlled by adsorbed proteins and is receptor mediated. Fibronectin (FN), was the first cell adhesion molecule (CAM) that was shown to be involved in the adhesion of some avian and mammalian cell types to extracellular substrates (3, 4). FN is commonly provided to the in vitro environment through the addition of serum, in a form known as cold-insoluble globulin (CIg). For normal attachment and spreading of cells to occur, it was found that CIg had to be adsorbed to the culture surface (5, 6).

FN consists of several protease-resistant domains, each of which contain specific binding sites for other extra cellular molecules and for the cell surface (7). The cell attachment activity has been localized to a tripeptide sequence (RGD), located in the cell binding domain of FN as well as in several other CAMs (8). Substrate-bound, RGD-containing peptide, directly adsorbed to the substrate, or peptide cross-linked to adsorbed albumin or IgG, was found to promote fibroblast attachment and spreading. This attachment and spreading activity was found to be readily inhibited by the addition of soluble RGD-containing peptides to the medium (8).

Affinity chromatography of cellular extracts on cell attachment-promoting FN fragments combined with specific elution utilizing synthetic RGD-containing peptides yielded a receptor with two 140 kD subunits (9). The mammalian FN receptor and other RGD directed receptors are typically heterodimers of two subunits, alpha and beta (10). Families of these receptors consist of members with similar beta subunits, whereas the alpha subunits are more distinct and restrict the receptor's affinity to one or a few CAMs (11). Collectively, these structurally and functionally related receptor families are known as the integrin superfamily (12, 13).

A basic understanding of the molecular mechanisms underlying the process of cell adhesion has thus developed regarding the role of the cell culture substrates and other surfaces in promoting cell adhesion. Basically, after a protein solution is placed on a culture substrate, proteins are immediately adsorbed to the surface. If there are receptors for some of these adsorbed proteins on the cell surface, and if the conformation of the adsorbed protein is not so extensively altered by adsorption as to destroy the high ligand-receptor affinity, then cell adhesion to the culture substrate and cell spreading can result.

If the cells are seeded on a substrate in the absence of adsorbed proteins, then the proteins on the cell surface may directly adsorb to the surface and the cell will, provided favorable conditions, secrete its own proteins toward the surface in the form of an extracellular matrix. However, if the substrate does not support protein adsorption, or if it supports high affinity adsorption of a protein for which there is not a cell-surface receptor, then the substrate will not support cell adhesion. In no case has the cell in culture been found to actually touch the surface except through these intermediate adsorbed proteins.

Some investigators who study short-term cell adhesion have proposed the use of substrate treating systems which promote cell adhesion wherein particular peptides are adsorbed to a polymer surface. For example, Singer, et al. proposed the adsorption of a 13-mer peptide containing the RGD sequence onto a polymer substrate to promote cell adhesion (14). However, peptides of this length have been found to be highly susceptible to degradation at high temperatures and to the proteolytic action of the cultured cells themselves. Additionally, peptides adsorbed to a surface are subject to desorption upon repeated use. Thus, surfaces with long amino acid residue peptides absorbed thereto have been found to be unstable and thus unsuitable in preparing reusable cell culture substrates.

An alternative approach in promoting cell adhesion is through chemical modification of the surface to facilitate the attachment of peptides to the substrate. However, present technology for chemical modification of substrates is particularly non-specific and empirical. For example, treatment of polymer surfaces with various radio frequency plasma discharges, both polymerizing and nonpolymerizing, has been proposed. Alternative approaches of surface acid treatment or surface incorporation of charged groups have also been described. However, these various surface treatments alter only the pattern of protein adsorption on the culture surface, which in turn functions to modify the cells' characteristic adhesion and spreading behavior. Thus, the protein and peptide surface adsorption and desorption problems still remain, limiting the reusability of culture plates and other surfaces so treated.

An alternative to surface adsorption of peptides to promote cell adhesion has been to instead chemically attach peptides to a surface. For example, the method of polymer surface chemical modification was employed by Brandley, et al., (1988) (*Analyt. Biochem.* 172: 270), who proposed the inclusion of a 9-mer peptide in a polymer substrate to promote cell adhesion (Id.). While enhanced cell adhesion was attained using the Brandley technique, the method required higher concentrations of peptide to promote the same level of cell adhesion observed in the relatively more peptide efficient adsorbed peptide systems. For example, FIG. 1 of Brandley shows surface concentrations of peptide on the average of about 6 nanomoles per square centimeter (Brandley, at pg. 275). These high peptide concentrations suggest the Brandley method does not control for the inclusion of peptide at the polymer surface only, but instead permits the incorporation of peptide throughout the bulk of the polymer. Given that synthetic peptides cost about $5,000 per gram, this method would not facilitate the economical preparation of cell culture substrates commercially.

Thus, a need still exists in the art for an economical system of preparing thermally stable, peptide-coated surfaces with cell adhesion promoting characteristics which are resistant to the desorptive effects of repeated usage and proteolysis by cellular proteases or proteases added to remove cells. A more commercially feasible and economical system would be substantially more peptide-efficient than those proposed by Brandley and others of skill in the art of cell culture and polymer chemistry.

The following abbreviations are used by Applicants throughout the application:

D = Asp (aspartic acid)
F = phenylalanine
G = Gly (glycine)
I = Ile (isoleucine)
R = Arg (arginine)
S = Ser (serine)
Y = Tyr (tyrosine)
CFN = cellular fibronectins
FC = focal contacts
FEP = fluorinated ethylene polymers
fg = fibrinogen
GREDV = glycine, arginine, glutamic acid, aspartic acid, valine or Gly-Arg-Glu-Asp-Val
GRGD = amino acid sequence glycine, arginine, glycine, aspartic acid; or Gly-Arg-Gly-Asp
HFF = human foreskin fibroblast cells
kD = kilodalton
mer = amino acid residue
nm = nanomoles
PAE = porcine aortic endothelial (cells)
PBS = phosphate buffered saline
PDMS = poly(dimethyl siloxane)
PET = poly(ethylene terephthalate)
pFN = plasma fibronectins
PHEMA = poly(hydroxyethyl methacrylate)
PTFE = poly(tetrafluoroethylene)
REDV = arginine, glutamic acid, aspartic acid, valine or Arg-Glu-Asp-Val
RGD = amino acid sequence arginine, glycine, aspartic acid, or Gly-Arg-Gly-Asp
SAM = surface adhesion molecule
ug = micrograms
ul = microliter
YIGSR = tyrosine, isoleucine, glycinem serine, aspartic acid or Try-Ile-Gly-Ser-Arg

SUMMARY OF THE INVENTION

The present invention features a new process by which surfaces may be modified to yield proteolytically stable, reusable surfaces which promote the amount of and enhance the rate of receptor mediated cell adhesion. The specifically directed and controlled chemical processes herein disclosed provide for the chemical attachment of peptides at the surface of a flask or other device without diffusion of the peptide throughout the bulk of the material treated. Thus, the disclosed methods provide a surprisingly enhanced cell adhesion promoting surface with the use of only a fraction of the peptide required by formerly proposed methods. The peptides are chemically attached to a surface, and thus avoid the desorbtion problems which plagued surface peptide-adsorbed systems of the past. These advantages are accomplished through the chemical attachment of small peptides, for example, those having less than 12 amino acid residues, at only the surface of the substrate.

An additional feature of the present invention lies in that the process provides for the use of cell adhesion molecule fragments, rather than whole surface adhesion molecule (SAM) proteins. The acronyms SAM and CAM are used interchangably to denote surface, substrate or cell adhesion molecules that are proteins which interact with extracellular matrix components through a specific binding domain to promote specific domain-mediated adhesion of cell receptors (i.e., the cells). SAMs are a family of proteins that include fibronectin, vibronectin, thrombospondin, laminin, and other proteins. Grafting of small peptide fragments provides a further advantage in that surfaces so treated are less subject to denaturation and proteolytic degradation than surfaces grafted with whole proteins or larger peptides.

A further feature of the present invention is that it provides a more efficient surface modification system. For example, Applicants are able to produce a derivatized surface with maximal cell adhesion properties using only 1/500th the amount of peptide of formally proposed chemical grafting methods. For example, Brandley, et al. employed a method which yielded on the average of 6 nanomoles/cm$^2$ (6,000 picomoles/cm$^2$) peptide surface concentration (Brandley, et al., pg. 274, Table 1). In contrast, Applicants have demonstrated enhancement of cell adhesion with a surface peptide concentration of as little as 0.0012 picomoles/cm$^2$ (a five million fold improvement). Applicants were able to omit a significant amount of the surface peptide in the process of chemically binding a peptide to a surface, and were able to achieve such without a loss in cell adhesive promoting activity.

An additional feature of the disclosed surface modification techniques is that they provide a novel approach for promoting receptor-mediated cell attachment independent of adsorbed serum components. The present invention provides a method for the treatment of surfaces which is effective in promoting the adhesion of any species and type of cell, including for example, porcine, murine and human cells. Types of cells which have already been successfully cultured on the treated surfaces include aortic, foreskin and 3T3 fibroblast cells (ATCC #CRL1658).

The present invention also features adaptability of use with a wide variety of small peptides. While numerous small peptide may be used in conjunction with the present invention, the most preferred small peptides include those with less than 12 amino acid residues (12 mer). More preferably, these peptides contain between 3-9 amino acid residues (3-9 mer). The most preferred peptides have either 6 amino acid residues (6 mer) or 4 amino acid residues (4 mer). The number of amino acid residues in a peptide are are often denoted herein by such nomenclature (e.g., 6 mer, 4 mer, etc.).

These small peptides are further described as including a minimal cell-surface receptor recognition sequence, for example, RGD, YIGSR, or REDV. This sequence permits the cell receptor mediated support of cells to a treated surface. By way of example, the most preferred peptides which include the about minimal cell surface receptor recognition sequences include the GRGD (Gly-Arg-Gly-Asp), GYIGSRY (Gly-Tyr-Ile-Gly-Ser-Arg-Tyr), GYIGSR (Gly-Tyr-Ile-Gly-Ser-Arg), GRGDY (Gly-Arg-Gly-Asp-Tyr), YIGSR (Tyr-Ile-Gly-Ser-Arg), RGD (Gly-Arg-Asp), REDV (Arg-Glu-Asp-Val), GREDV (Gly-Arg-Glu-Asp,Val), RGDS (Arg-Gly-Asp-Ser), GRGDS (Gly-Arg-Gly-Asp-Ser), RGDF (Arg-Gly-Asp-Phe), GRGDF (Gly-Arg-Gly-Asp-Phe) amino acid sequences. These fragments contain either the cell attachment sequence of many surface adhesion molecules (RGD) or the cell attachment sequence of laminin (YIGSR), a particular surface adhesion protein, or the cell adhesion molecule fibronectin (REDV). These most preferred peptides may further include a C-terminal Y for radioiodination. The N-terminal G is used as a spacer with the particular peptide between the adhesive peptide and the surface. The small peptides are used to provide cell receptor recognition sites required for cell adhesion on the treated surface.

While any surface concentration of peptides of at least 1 picomole/cm$^2$ is expected to be sufficient to enhance the cell adhesive characteristics of a surface, a more preferred range of peptide surface concentration is between about 0.5 to 100 picomoles/cm$^2$. A more preferred range of peptide surface concentration is 0.5 to 20 picomoles/cm$^2$. The most preferred peptide surface concentration of the present invention is about 12 picomoles/cm$^2$.

Conventional methodologies rely upon direct adsorption of the CAM or the peptide to the surface, or adsorption of non-CAM proteins followed by cross-linking of the peptides to the adsorbed proteins, thus allowing for desorption of these components into the culture media. The present invention provides the further advantage of avoiding this problem of protein desorption by chemically bonding the peptide through covalent bonds to hydroxyl or other reactive moieties of the desired substrate.

There are many situations in the use of biomedical implants where it is desirable that the surrounding cells in the tissues adhere to and spread upon (integrate with) the implant surface. The present invention provides a method for surface modification to obtain such desired implant integration within the host. The present invention further features a method for reducing the incidence of infection attendant to the in vivo implant of biomedical devices. A major risk associated with implantation of biomedical devices has been infection. The lack of a continuous protective layer between the device and the biological tissue opportunizes the entry of bacteria and other infectious agents into the tissue. With the enhanced cell adhesion promoting surface as part of the device, such undesirous side effects will be minimized, as a continuous protective cell covering is provided, closing the potential entry of infectious agents.

Additionally, the long-term stability of the disclosed treated surface method makes the system ideal in preparing various biomedical implants for extended term body emplacement. For example, in use with nerve growth guides and indwelling catheters. The surface modification system of the present invention also provides new avenues for mammalian cell bioreactor design, since it provides a stable integral surface component which supports cell adhesion independent of media CAMs. Such substrates provide the further advantage of permitting the use of serum-free media which are deficient in cell adhesion molecules.

The chemistry of the present invention is directly applicable to any material with surface hydroxyl moieties or other surface reactive groups to which such moieties can be added. Most other surface treatments to enhance cell adhesion do so by the enhancement of protein absorption. The peptide grafting approach of the present invention eliminates the requirement for absorbed proteins completely, as the cell has receptors for the surface-coupled synthetic peptides. These covalently bound minimal sequences are much more stable to cellular proteolysis and thermal degradation than adsorbed cell adhesion proteins or adsorbed proteins conjugated with adhesion peptides, since desorption is eliminated and the active groups (e.g. RGD, YIGSR or REDV sequence) are not as exposed to soluble proteases.

While a variety of chemical methods exist by which the present surfaces may be prepared, the various approaches fall into the general class of surface activation, via modification of a nucleophile, such as an amine or hydroxyl, followed by coupling to the peptides, via another nucleophile such as an amine or hydroxyl (23). By way of example, the activation of surface hydroxyl groups may be accomplished through treatment with agents such as tresyl chloride, glutaraldehyde, cyanuric chloride, sulfonyl chlorides, cyanogen bromide and benzoin dimethyl sulfoxide with potassium tert-butoxide in dimethyl sulfoxide. Treatment with these particular surface activators is followed by a procedure by which a peptide is covalently linked to the hydroxyl group. Additionally, the present invention may be practiced through the production of active carboxyl groups on the surface by using, for example, succinic anhydride. The exposed surface is then rinsed and coupled with peptide.

By way of example, biomedical implants which would benefit from the inclusion of the present surface peptide treatment include penile, heart, vaginal, and hip implants; catheters; artificial veins or arteries, artificial tendons and, ligaments; artificial bone screws, bone plates, bone fragments and bone joints; artificial skin; nerve growth guides; and intraocular lenses and the like. By way of example, materials used as cell and tissue culture substrates which profit from the present surface peptide treatment include tissue culture flasks, petri dishes, microcarrier beads, porous macrocarriers, fibers, hollow fibers, monolith supports, and roller bottles.

The disclosed methods may be used in the derivatization of any surface to which enhanced cell adhesion is desired. By way of example and not limitation, these surfaces include metal, ceramic or polymer surfaces. A preferred embodiment of the invention is directed to the derivatization of polymer surfaces. While any polymer surface may be derivatized using the proposed methods, particular exemplary, polymer surfaces most preferably include poly(hydroxyethyl methacrylate) (PHEMA), poly(ethylene terephthalate) (PET), poly(tetrafluoroethylene) (PTFE), fluorinated ethylene (FEP), poly(dimethyl siloxane) (PDMS) and other silicone rubber surfaces. PET, otherwise known as Dacron, is a polyester frequently used for biomedical implants. PTFE is otherwise known as Teflon. Most preferred polymeric matrix of the present invention comprises poly(hydroxyethyl methacrylate) (PHEMA).

The PHEMA polymeric matrix comprises a gel-like matrix having about a 45% water composition, and was, prior to the disclosure of the present invention, unable to support cell adhesion.

Use of peptides in conjunction with other high-water polyacrylamide gel matrixes is much less peptide-efficient compared to such use with polymers of lower water content. Highly hydrated gels are highly permeable to peptides and thus facilitates the substantial and indiscriminant diffusion of small peptides into the bulk of the polymer. These highly hydrated polymers have been used for protein electrophoresis, demonstrating that they are even permeable to whole proteins, which are very large molecules (21). Polymer gels comprising polyacrylamide include about 90% water, and, thus would be unsuitable in the practice of the present invention.

Another most preferred embodiment of the invention is directed to the derivitization of a particular ceramic, glycophase glass (glycerol propylsilane bonded glass). By way of example, a most preferred metal to be used with the lo described process is titanium.

The present invention also includes methods of enhancing cell adhesion to a surface comprising first activating the surface, coupling a peptide to the activated surface, and then plating mammalian cells on the peptide derivatized surface, wherein the preferred peptide is smaller than a 12 mer. The process whereby the peptide is coupled to any activated surface most preferably comprises exposing an activated surface to a solution containing a sufficient amount of the peptides described above (having cell-adhesive characteristics). While any concentration of peptide solution of at least about 10 ng/ml would produce equal results in the present coupling process, solutions between about 10 ng/ml peptide and 100 ug/ml peptide are also suitable. Most preferably, the process includes a peptide solution having a concentration of 10 ng/ml peptide. In one preferred embodiment of the invention, the peptide of the peptide solution includes the amino acid sequence arginine-glycine-asparagine (RGD). In another preferred embodiment of the invention, the peptide of the peptide solution includes YIGSR. In still another preferred embodiment of the invention, the peptide of the peptide solution includes REDV or RGDF. A most preferred peptide to be used in the method of the present invention comprises a peptide sequence selected from the group consisting of GRGD, RGDY, GRGDY, GYIGSR, GYIGSRY, YIGSR, RGDS, REDV, GREDV, RGDF and GRGDF. These peptides are most preferably used in the derivatization of polymer surfaces, such as PET polymer and PHEMA polymer, or glass surfaces, such as glycophase glass. However, any peptide which includes an amino acid surface capable of supporting cell receptor recognition may be used in conjunction with the present invention.

Applications of the bioactive cell adhesive peptide grafting approach to enhance cell adhesion include the following uses:

1. For laboratory scale tissue and cell culture of anchorage dependent cells and cell lines. This approach may be useful in the treatment of laboratory glassware and plasticware used as cell culture substrates, such as tissue-culture flasks and Petri dishes. It would be useful for animal, insect, and plant cells and tissues, as all utilize essentially the same molecular biology for adhesion.
2. For large scale tissue and cell culture. The approach may be useful in the treatment of microcarriers, porous macrocarriers, hollow fibers, monolith supports, and roller bottles.
3. For the interior of implantable artificial vascular grafts to promote the endothelialization of these surfaces.
4. For the exterior and anastamotic regions (ends) of vascular grafts to promote integration into the tissues.
5. For other implantable devices where integration with the tissues is desirable, such as artificial tendons, ligaments, bone screws and plates, bone fragments, joints, and skin.
6. For the treatment of sutures to promote adhesion with and integration to the tissues.
7. For the promotion of directional growth or migration of cells or tissues, this approach may be useful when the peptides are grafted to the surface with a gradient of surface concentration. An example where this may be useful is in nerve growth guides for peripheral nerve regeneration.
8. For use in research. The present systems allow for the study of cell adhesion in the presence of serum without the confusion of the effects of protein adsorption. Thus, background levels in the test system remain low. Additionally, the present methods control for the amount of peptide which gets coupled to a surface, which is also important in studying cell adhesion.

DETAILED DESCRIPTION OF THE PREFERRED EMBODIMENTS

Figure 1:
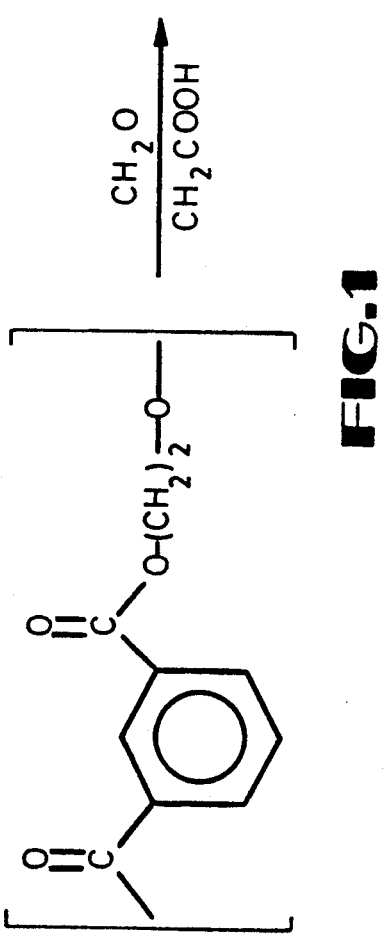
FIG. 1 shows the hydroxymethylation of PET films via electrophilic aromatic substitution. The reaction was carried out at room temperature with 18.5% formaldehyde (v/v) and 1M acetic acid.

The present invention is directed toward treated surfaces and methods of preparing treated surfaces which enhance cell-surface adhesion thereto independent of adsorbed peptides and soluble media components. This methodology provides techniques for preparing various types of substrates which simplify optimization of culture systems and which also improve the amount and rate of cell bioadhesion to surfaces of various materials.

More particularly, the surface modification techniques provide for the chemical grafting of peptides to a surface, the peptide comprising at least the minimal amino acid sequence included in a cell (surface) adhesion molecule, such as RGD in fibronectin, or YIGSR in laminin, REDV in some forms of fibronectin, or some other short peptide sequence related to or derived from the sequence of a protein involved in cell-surface or cell-cell adhesion. The terms "Cell Adhesion Molecule" (CAM), "Surface Adhesion Molecule" (SAM) and "Substrate Adhesion Molecule" (SAM) are used interchangeably in describing the family of proteins and peptides found to facilitate cell receptor-mediated adhesion or attachment to a surface.

The present surface treatment methods basically comprise chemically activating a surface to expose reactive groups, rinsing the activated surface, and then exposing the surface to a solution containing small peptides, for example, a peptide which includes the RGD, YIGSR, REDV, or other amino acid sequence which facilitates receptor mediated cell attachment having less than a total of 12 amino acid residues (12-mer). A covalent chemical bond attaches the terminal end of the peptide to a reactive moiety on the surface being treated. A variety of chemical methods exist by which a surface may be activated to expose reactive groups. One of these methods is by way of the tresyl activation. Other alternative chemistries which may be used in the practice of the present invention, by way of example include:

(1) Activation of the surface with glutaraldehyde: At temperatures between 0° C. and 80° C., treat the surface with an aqueous solution of 5% to 37% glutaraldehyde for about one hour. The glutaraldehyde will couple with any exposed nucleophilic groups, such as amines and hydroxyls. Rinse the surface with water, and treat the surface with a solution of peptide, between 10 ng/ml and 1 mg/ml. Any nucleophilic groups on the peptide, such as thiols, amines, and hydroxyls, will be coupled to the surface-coupled glutaraldehyde function.

(2) Activation of the surface with cyanuric chloride: At temperatures between 0° C. and 80° C., treat the surface with a nonaqueous solution of about 5% cyanuric chloride for about one hour. The cyanuric chloride will couple with any exposed nucleophilic groups, such as amines and hydroxyls. Rinse the surface with dry solvent, and treat the surface with a solution of peptide, between 10 ng/ml and 1 mg/ml in a nonaqueous solvent, such as acetonitrile. Any nucleophilic groups on the peptide, such as thiols, amines, and hydroxyls, will be coupled to the surface-coupled cyanuric chloride function.

(3) Activation of the surface with other sulfonyl chlorides: Follow the procedure outlines in Example 3 using another member of the sulfonyl chloride family, such as tosyl chloride.

(4) Activation of the surface with cyanogen bromide: At temperatures about 20° C. or below, expose the surface to an aqueous solution of cyanogen bromide at pH 10-11 for about one hour. The cyanogen bormide will covalently couple and activate surface hydroxyl groups. Rinse the surface with water at pH 10-11, and couple with peptide between 10 ng/ml and 1 mg/ml in this same solution for about 1 hour. The peptide will couple to the cyanogen bormide groups via any amine functions on the peptide.

(5) Activation of the surface to produce active carbonyl-bearing esters, e.g. with succinic anhydride: At temperatures of about 20° C., expose the surface to a solution of succinic anhydride, whereupon that compound will react with surface hydroxyls and amine to produce esters and amides, respectively. Rinse the surface and couple with peptide between 10 ng/ml and 1 mg/ml for about 1 hour. The peptide will react with the activated surface via amine or hydroxyl groups.

(6) Preactivating a polymer by adding hydroxyls with benzoin dimethyl sulfoxide: Hydroxyl functions are added to poly(tetrafluoroethylene) (PTFE). As described by Costello and McCarthy, Surface-Selective Introduction of Specific Functionalities onto Poly(tetrafluoreoethylene), *Macromolecules* 20:2819-2828 (1987)). Benzoin dimethyl sulfoxide is added to a solution of potassium tert-butoxide in dimethyl sulfoxide and placed in contact with the PTFE surface. The reaction is allowed to proceed at 50° C. for 1 hour. The material is removed and rinsed with tetrahydrofuran (THF). This intermediate surface is then treated with 1M borane in THF at room temperature for 12 hours. The surface is then treated with 1M NaOH containing 10% hydrogen peroxide at 0° C. for 3 hours, after which it is washed sequentially with dilute NaOH, water, dilute HCl, water, THF, and heptane. This produces a surface that is rich in hydroxyls and can subsequently be activated by any of the chemistries described above.

The most preferred method by which peptides are attached to a surface comprises surface activation of the surface, by a tresyl immobilization method, as described by Nilsson and Mosbach (1981) (*Biochem. Biophys. Res. Commun.*, 102: 449-457). Specifically, tresyl activation is a process wherein the surface is first immersed in 20 ml. dry ether containing about 40 ul 2,2,2-trifluoroethanesulfonyl chloride (tresyl chloride) and about 2 ml. triethylamine for about 15 minutes at room temperature. These activated surfaces were then rinsed with 0.2M sodium bicarbonate pH 10 buffer. The surfaces were then placed in the same buffer containing about 60-100 ng/ml of the peptide for about 20 hours at room temperature. Most preferably, the concentration of peptide solution is about 10 ng/ml. This incubation time allows for the coupling of the peptide to the surface hydroxyl groups. This particular embodiment of the invention is preferably used with the GRGD peptide.

The peptides couple to an activated surface most preferably by exposing the activated surface to a solution containing an appropriate amount of the desired peptide. While any concentration of peptide solution of at least about 10 ng/ml would produce equally satisfactory results, solutions containing between about 10 ng/ml peptide and 100 ug/ml peptide are preferred. Most preferably, a peptide solution of about 10 ng/ml peptide is used in the coupling process.

The treated surfaces produced by the disclosed methods are characterized by a peptide surface concentration of at least 1 picomole/cm$^2$. It is expected peptide surface concentrations of at least 1 picomole/cm$^2$ are sufficient to enhance the cell adhesive characteristics of a surface. A more preferred range of peptide surface concentration is between about 0.5 to 100 picomoles/cm$^2$. A most preferred range of peptide surface concentration is between about 0.5 to 20 picomoles/cm$^2$. The most preferred surface peptide concentration is about 12 picomoles/cm$^2$.

Where no surface hydroxyl moieties exist on the surface to be treated, the surface was pretreated. This pretreatment preferably comprised a surface hydroxylation procedure wherein an electrophilic aromatic substitution was employed to add hydroxyalkyl groups to a surface. A particularly preferred method of this pretreatment comprises immersing a surface in an about 18.5% (v/v) solution of formaldehyde and about 1M acetic acid for about 4 hours at room temperature. This procedure was used in the hydroxymethylation of a particularly preferred embodiment of the invention comprising a PET polymer surface. The hydroxylated surface was then tresyl activated with the attachment of peptides thereto as described above. Most preferably, the pretreatment method disclosed herein is used to prepare polymer surfaces, particularly PET polymer surfaces, With GRGD or GYIGSR peptides. Various other surface hydroxylations would be equally as useful for use in conjunction with other polymers or materials. Various other linking characteristics may also be used, where the N-terminal amine or another reactive group on the peptide is reacted with a group on the surface, perhaps with the use of some linker.

Any surface may be used in the practice of the present invention. By way of example, surfaces particularly suitable for use in the practice of the present invention comprise a ceramic, a metal, or a polymer surface. Most preferably, the present invention is used in the treatment of polymer surfaces and ceramic (glass) surfaces. By way of example, the polymer surfaces comprise poly(-hydroxyethyl methacrylate) (PHEMA), poly(ethylene terephthalate) (PET), poly(tetrafluoroethylene) (TPFE), fluorinated ethylene (FEP), poly(dimethyl siloxane) (PDMS) and other silicone rubbers. While a variety of glass surfaces may be treated with the proposed methods, the glass surface most preferred comprises glycerol propylsilane bonded glass (glycophase glass).

A minimal amino acid sequence included in many cell adhesion molecules is RGD (arginine-glycine-aspartic acid amino acid sequence), or YIGSR (tyrosine-isoleucine-glycine-serine-arginine) or REDV (arginine-glutamic acid-aspartic acid-valine). While any peptide containing a minimal amino acid sequence active in cell adhesion may be used in the practice of the present invention, those sequences most preferred comprise RGD, YIGSR, GRGD, GYIGSR, GRGDY, GYIGSRY, RGDY, YIGSRY, REDV, GREDV, RGDF and GRGDF.

In a particularly preferred embodiment of the present invention, the peptides GRGDY and GYIGSRY are chemically grafted to a surface of glycerol propylsilane bonded glass (glycophase glass) a specific type of ceramic. The C-terminal Y of these preferred peptides is included for radio iodination, the N-terminal G (glycine) is provided for use as a spacer with the particular peptide between the adhesive peptide and the surface. The small peptides are used to provide cell receptor recognition sites required for cell adhesion on the treated surface.

In another particularly preferred embodiment of the present invention, the GRGD and GYIGSR peptides are used in the chemical derivatization of polymer surfaces. A most preferred embodiment of the present invention comprises a PHEMA or PET polymer surface derivatized with GRGD or GYIGSRY peptides. Another even more most preferred embodiment of the present invention comprises a PHEMA or PET polymer surface derivatized with GYIGSRY peptides.

A surface so treated to include covalently bound peptide provides mammalian cell receptor recognition sites which allow the cells to anchor to the substrate and grow independent of media serum content and surface adsorbed proteins. Thus, the present invention discloses methods which provide for receptor-mediated cell adhesion in the absence of any intermediate adsorbed protein, i.e., an entirely self sufficient cell adhesion and spreading supportive surface.

While any peptide fragment which includes the minimal amino acid sequence of the cell adhesion molecule may be used in the practice of the present invention, peptide fragments containing less than 12 amino acid residues (mer) are preferred. Peptide fragments having between about 3-9 amino acid residues are even more preferred. The most preferred peptides include either 4 or 6 amino acid residues. The length of the peptide fragment will affect the susceptibility of the peptide to degradation, and therefore, the shorter the fragment, the less peptide surface degradation would be expected.

The present invention further includes surface-treated biomedical implant devices and methods for preparing the same. Devices having such surface treatments enhance the amount and rate of cell adhesion, and thus the rate of tissue integration of the device in vivo. Enhanced cell adhesion and tissue integration act to minimize infection, as potential tissue ports of entry are "sealed" closed by a protective layer of cells.

Any device surface to which the described peptides may be chemically grafted can be treated with the described methods. By way of example, these device surfaces include those of penile, vaginal, heart and hip implants or replacements; catheters; artificial skin, veins and arteries; artificial tendons and ligaments; artificial bone screws, plates, fragments and joints; nerve growth guides; intraocular lenses and the like.

Applicants' present evidentiary material herein which demonstrate the cell adhesive properties imparted to a surface treated with the disclosed peptides and methods of the present invention. The treated surfaces are suitable for the culture of any species and type of cell including, for example, porcine, murine, insect and human cells. Applicants have used a variety of cells in demonstrating the present invention, including, by way of example and not limitation, foreskin fibroblast (HFF) cells, aortic endothelial (PAE) cells, embryotic and newborn tissue cells. However, the present invention may be used in conjunction with any species or tissue source of cell, and is not limited to use with any one particular type of cell. The following paragraphs outline the most preferred methods of culturing particular cell types used to demonstrate the present invention.

CELL CULTURE PROCEDURES

3T3 Cells

NIH/3T3 cells, an immortal cell line of embryotic cells established from Swiss mouse embryos, were obtained from the American Type Culture Collection cell repository (ATCC #CRL 1658). Cultures were maintained in Dulbecco's modified Eagle's medium supplemented with 10% fetal calf serum and incubated at 37° C. in a humidified 5% $CO_2$ atmosphere. Confluent monolayers of cells were harvested by incubation in a solution of 0 5% trypsin and 0.53 mM EDTA in phosphate buffered saline (PBS) at 37° C. for 15 minutes. Cells were resuspended in fresh medium and subcultivated by allowing cells to attach and grow to in new culture dishes.

Human Foreskin Fibroblasts

Human foreskin fibroblasts (HFFs) are primary cell lines that are isolated from neonatal foreskin tissue from Seton Hospital, neonatal ward, Austin, Tex. About 5–10 newborn foreskins are collected aseptically in sterile PBS, minced into 5 $mm^2$ pieces, and incubated in trypsin-EDTA for 4 hours. HFFs were collected by centrifugation at 200 g for 5 minutes and resuspended in Dulbecco's modification of Eagle's medium (DMEM, Mediatech) supplemented with 10% fetal calf serum (GIBCO), 400 u/ml penicillin (Irvine) and 400 ug/ml streptomycin (Irvine) and incubated at 37° C. in a humidified 5% $CO_2$ atmosphere. Cells were subcultivated by trypsinizing confluent monolayers, suspending cells in fresh medium, and seeding cells into new flasks. HFFs were maintained in culture for up to 20 passages before they are discarded.

Porcine Aortic Endothelial Cells

Porcine endothelial cells were obtained from sacrificed miniature swine. The endothelial cells were isolated by the method of Jaffe, et al. (1973, *J. Clin. Invest.*, 52: 2745–2756). Specifically, porcine aorta tissue segments from sacrificed miniature swine were rinsed with warm (37° C.) PBS to remove blood and placed in 10 cc syringes. The lumen of the segments were then filled with a 100 ul/ml solution of Sigma Type II collagenase. The tissue was then incubated for 30 min. at 37° C. The lumen of the aorta was then washed with PBS, and the cells were centrifuged at 200 g for 5 mins. and resuspended in Medium 199 supplemented with 20% fetal calf serum and antibiotic. The suspension was added to culture flasks and the cultures were maintained at 37° C. in a humidified, 5% $CO_2$ atmosphere.

The following examples are presented to describe preferred embodiments and utilities of the present invention and are not meant to limit the present invention unless specifically indicated otherwise in the claims appended hereto.

Example 1 describes the method by which particularly preferred peptide fragments were synthesized, Example 2 describes the derivatization of a PH(MA polymer surface, Example 3 describes the derivatization of a PET polymer surface, Example 4 describes the preferred method of preparing a primary cell culture from foreskin tissue, Example 5 describes the adhesion of cells to a derivatized PHEMA and PET polymer surface.

Examples 6, 7 and 8 describe the derivatization of a glass surface, the cell adhesive and supportive characteristics of such a derivatized glass surfaces and the comparative cell supportive characteristics provided by various peptides to a derivatized verses non-derivatized glass surface. Example 9 describes the relative stability of a derivatized PET polymer and glycophase glass surface to heat and proteolysis. Example 10 presents a comparative study on the cell supportive characteristics of a pretreated verses a non-pretreated PET polymer surface. Examples 11 and 12 demonstrate proposed methods of using the described surface derivitization processes with a biomedical implant (Example 11—indwelling catheter; Example 12—nerve growth guide).

EXAMPLES

Example 1—Small Peptides

This example demonstrates particularly preferred methods of synthesizing peptides having less than 12 amino acid residues and including at least the amino acid sequence arginine-glycine-aspartic acid (RGD). This sequence is a particular minimal cell attachment sequence recognizable by cells in cell-receptor mediated cell adhesion.

The peptides used in these studies, GRGD, GRGE, GYIGSR, GRGDY, GRGEY, and GYIGSRY, were synthesized by known procedure at the University of Texas Southwestern Medical School peptide synthesis laboratory.

Example 2—Preparation of Phema Polymer Surface

This experiment was designed to describe one particularly preferred method of preparing a polymer surface with small peptide fragments covalently attached thereto. PHEMA (poly(hydroxyethyl methacrylate)), is a hydrogel which has been found unable to support cell adhesion in its untreated state.

The particularly preferred peptides GRGD and GYIGSR were grafted to the polymer surface rising the PHEMA surface hydroxyl groups and the terminal primary amine of the glycine linker arm of the peptide using tresyl chloride activation. The G group at the terminal end of each respective peptide was used to add distance between the surface-active peptide (GRGD) and the polymer surface.

More particularly, the coupling method utilized activation of PHEMA surface hydroxyl moieties by tresyl chloride in an organic solvent for the reaction components but a nonsolvent for the polymer. PHEMA films did not require pretreatment, since their surfaces are amply supplied with hydroxyethyl groups. The cell adhesive promoting activities of this modified surface were determined as outlined in Example 4, where in vitro cell adhesion and spreading assays were performed. The tresyl leaving group was then displaced in an aqueous solvent by the terminal amine of the peptide GRGD or GYIGSR.

The unmodified PHEMA films were then tresyl activated in 20 ml dry ether containing 20 ul of 2,2,2-trifluoroethanesulfonyl chloride (tresyl chloride) and 2 ml of triethylamine for 15 minutes at room temperature. Activated films were then rinsed with 0.2M sodium bicarbonate pH 10 buffer and placed in the same buffer containing 80 ng/ml GRGD for 20 hours at room temperature to couple the peptide.

Example 3—Preparation of Poly(Ethylene Terephthalate) (PET) Polymer Surface

This experiment was designed to describe one particularly preferred method of preparing a surface devoid of hydroxyl moieties so as to facilitate the inclusion of small peptides thereto to promote cell adhesion.

The PET surface is a polymer which is devoid of hydroxyl moieties, and therefore the surface must be pretreated before the surface is thereafter modified with a peptide. Specifically, the PET film surface was modified via an electrophilic aromatic substitution which added hydroxymethyl groups to the surface. The reaction was carried out at room temperature and atmospheric pressure. The films were then immersed in 18.5% (v/v) formaldehyde and 1M acetic acid for about 4 hours. The pretreated pET surface Was then modified exactly as described for the pHEMA surface as outlined in Example 2.

The following listing presents the most preferred method of pretreating a polymer surface, such as a PET matrix, which does not include hydroxyl moieties. The surface modification of hydroxyl moieties and attachment of peptides fragments thereto was accomplished with the following protocol:

1. Addition of surface hydroxymethyl moieties—to the PET polymer surface by performing an electrophilic aromatic substitution of surface groups or the polymer surface, wherein the PET polymer is immersed in 18.5% (v/v) formaldehyde and 1M acetic acid for 4 hours at room temperature.

2. Tresyl Activation—of surface hydroxyl moieties wherein the pretreated PET film is immersed in 20 ml. dry ether containing 40 ul of 2,2,2-trifluoroethanesulfonyl chloride (tresyl chloride) and 2 ml. of triethylamine for 15 minutes at room temperature.

3. Rinse—activated PET film was then rinsed with 0.2M sodium bicarbonate pH 10 buffer at room temperature to couple the peptide.

4. Peptide Coupling to Surface—rinsed PET films were then placed in the same buffer containing 80 mg/ml GRGD or GYIGSR peptide for 20 hours.

Example 4—Primary Cell Culture From Human Foreskin Tissue

Human foreskin fibroblasts (HFFs) are primary cell lines that were isolated from neonatal foreskin tissue from Seton Hospital, Neonatal Ward, Austin, Tex. The following procedure was used to establish primary cell lines from these tissues: 5-10 foreskins were collected aseptically in sterile PBS, minced into 5 mm² pieces, and incubated in trypsin-EDTA for 4 hours. HFFs were collected by centrifugation at 200 g for 5 minutes and resuspended in Dulbecco's modification of Eagle's medium supplemented with 10% fetal calf serum. Cells were subcultivated by trypsinizing confluent monolayers, suspending cells in fresh medium, and seeding cells into new flasks. HFFs were maintained in culture for up to 20 passages before they were discarded.

Example 5—Cell Adhesion Studies On Derivatized PHEMA and PET Polymer Surfaces

This experiment was designed to determine if a polymer surface could be designed and synthesized which would support receptor-mediated cell adhesion in the absence of any intermediate adsorbed proteins, i.e., to produce a surface that was entirely self-sufficient in its support of cell adhesion and spreading. Immobilization of entire proteins, such as collagen or fibronectin, can accomplish this but is associated with the difficulties of proteolysis, protein degradation, and protein denaturation. To circumvent this, the small, thermally stable peptide region of most CAMs, Arg-Gly-Asp (RGD) was covalently coupled to the surface of polymer films with a Gly N-terminal linker in the form of Gly-Arg-Gly-Asp (GRGD). This produced stable surfaces that were intrinsically bioadhesive, i.e., the material surfaces contained groups with a high affinity for cell-surface receptors completely independent of adsorbed CAMs from the culture medium. This surface modification provided a systematic methodology for developing well characterized substrata which simplifies optimization of a culture system. Mouse NIH-3T3 (ATCC #CRL 1658) fibroblasts were washed and innoculated in serum-free medium on both treated and untreated PHEMA substrata. Treated PHEMA substrata was prepared as outlined in Example 2.

CULTURE METHODS

NIH/3T3 fibroblasts (ATCC #CRL 1658, Rockville Md.) were cultured in DMEM supplemented with 10% calf serum in a humidified 5% carbon dioxide atmosphere at 37° C. Porcine aortas were obtained from sacrificed miniature swine. Endothelial cells were isolated by the method of Jaffe, et al. (1973, *J. Clin. Invest.*, 52: 2745-2756) with a modification to facilitate profusion of the lumenal surface of the vessel with collagenase. Porcine aortic endothelial cells (PAE) were maintained in DMEM supplemented with 10% fetal calf serum with the same incubation conditions as above.

Surface Modification Procedure

GRGD was grafted on polymer surfaces via the glycyl terminal amine using the tresyl chloride immobilization method of Nilsson and Mosbach and as described in Examples 3 and 4. Two polymer surfaces were modified, poly(hydroxyethyl methacrylate) (abbreviated PHEMA) and poly(ethylene terephthalate) (abbreviated PET). The coupling method utilized activation of surface hydroxyl moieties by tresyl chloride in an organic solvent for the reaction components, which is also a nonsolvent for the polymer. The tresyl leaving group was then displaced in aqueous solvent by the terminal amine of the peptide.

Poly(ethylene terephthalate) (P(T)) has no available hydroxyl groups for tresyl chloride activation, therefore a surface hydroxylation procedure was developed. An electrophilic aromatic substitution which adds hydroxymethyl groups to the PET films was employed (FIG. 1). Specifically, the commercially available PET films were immersed in 18.5% (v/v) formaldehyde and 1M acetic acid for four hours at room temperature, as particularly defined in Example 3. PHEMA films did not require pretreatment since their surfaces are amply supplied with hydroxyethyl groups.

Figure 2:
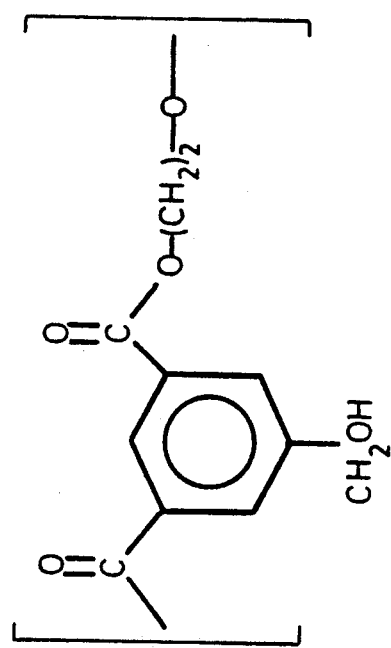
FIG. 2 shows the tresyl activation and GRGD coupling to hydroxymethylated PET films. All reactions were performed at room temperature.
Figure 2:
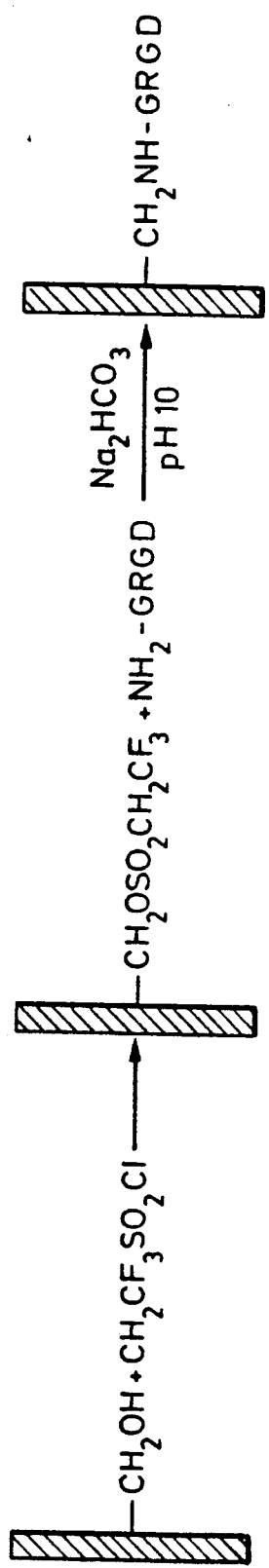

The modified PET and unmodified PHEMA films were tresyl activated in 20 ml dry ether containing 40 ul of 2,2,2-trifluoroethanesulfonyl chloride (tresyl chloride) and 2 ml of triethylamine for 15 minutes at room temperature. Activated films were then rinsed with 0.2M sodium bicarbonate pH 10 buffer and placed in the same buffer containing about 80 ng/ml GRGD for 20 hours at room temperature to couple the peptide. FIG. 2 graphically depicts a modified PET film with hydroxymethyl moieties and the subsequent steps involved with tresyl activation and GRGD coupling.

Cell Spreading Assay

Figure 3A:
FIGS. 3a and 3b show adherent and spread 3T3 fibroblasts on (a) GRGD coupled and (b) untreated PET films. Arrows indicate individual cells that were scored as spread cells. (200× Hoffman illumination).
Figure 3B:
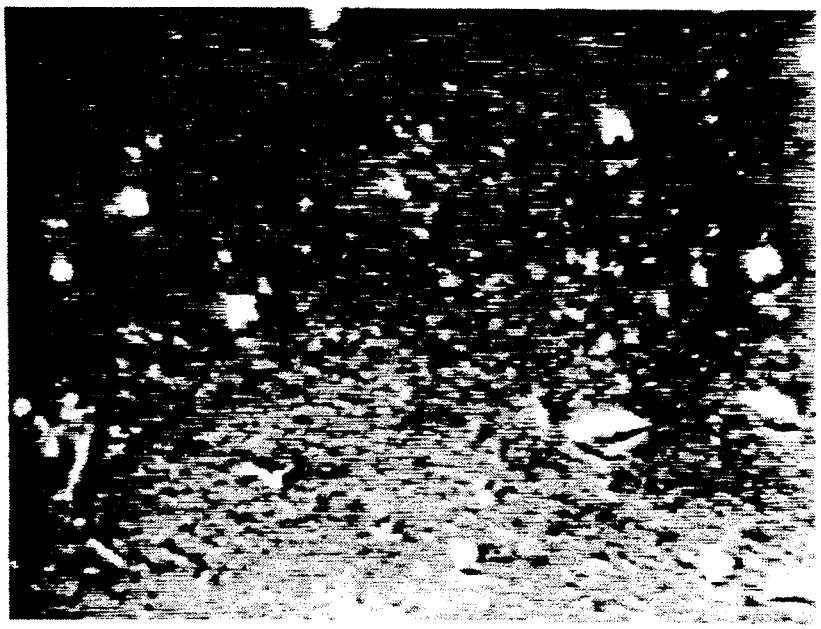

NIH/3T3 and PAE cells were detached from culture flasks by trypinsization and suspended in serum-free medium (DMEM with 1 mg/ml bovine serum albumin (BSA)). The cells were washed twice by centrifugation in the BSA containing medium and seeded at a density of 3,000 cells per cm² of film, unless otherwise noted, in serum-free medium and incubated in the normal culture environment. Spread cells were scored by morphological features such as distinct nuclei, pseudopodia, and polygonal shape (FIG. 3). Cells were visualized at $200\times$ magnification using Hoffman modulation contrast optics on a Leitz Fluovert inverted stage microscope. Cell growth was also assessed by determining spread cell counts at various time points, for cells cultured in media supplemented with 10% calf serum.

Actin Stress Fiber Visualization

NBD Phallacidin (7-nitrobenz-2-oxa-1,3-diazolyl-phallacidin) (Molecular Probes, Inc. Eugene, Ore.) was employed to visualize actin stress fibers and microfilament bundles in cells attached to the modified surfaces. Samples were prepared according to the manufacturer's procedure and $1000\times$ images were viewed utilizing the Fluovert microscope equipped with a Leitz E3 excitation filter and UV illumination.

Soluble Peptide Competition Studies

In the competition studies, 3T3 fibroblasts were preincubated for 30 minutes in either serum-free medium containing about 90 ug/ml RGDS or no peptide. The cells were then inoculated at a density of about 3000 cells/cm² on GRGD derivatized PET and spreading was determined after three hours incubation under normal culture conditions.

Figure 4:
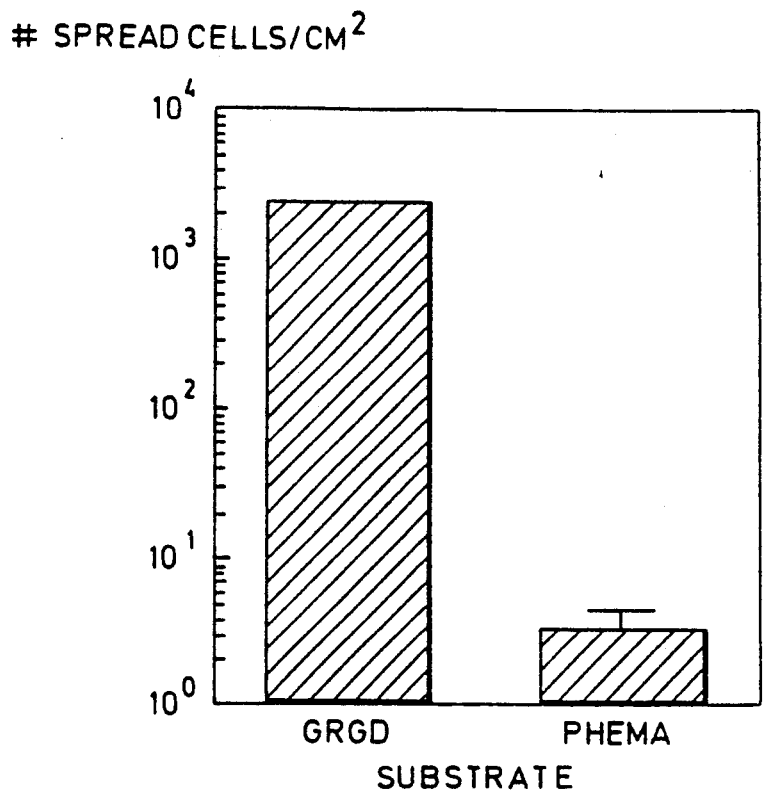
FIG. 4 shows the spreading of 3T3 fibroblasts on GRGD coupled and untreated PHEMA films in a serum-free culture medium. Extent of cell spreading was determined 3 hours after seeding of the substrates.

The GRGD derivatized substrates were characterized by their ability to support active adhesion of cells on their surfaces. The PET pretreatment was optimized by coupling GRGD to tresyl chloride activated films that were hydroxylated for various time periods. Cell spreading assays using NIH/3T3 fibroblasts were performed to determine conditions that supported a maximal response. Four hours pretreatment appeared to be optimal for maximum cell adhesion and spreading. PHEMA films were derivatized with GRGD utilizing low concentrations of peptide (80 ng/ml) which resulted in an increase in cellular adhesion by three orders of magnitude (FIG. 4).

Figure 5:
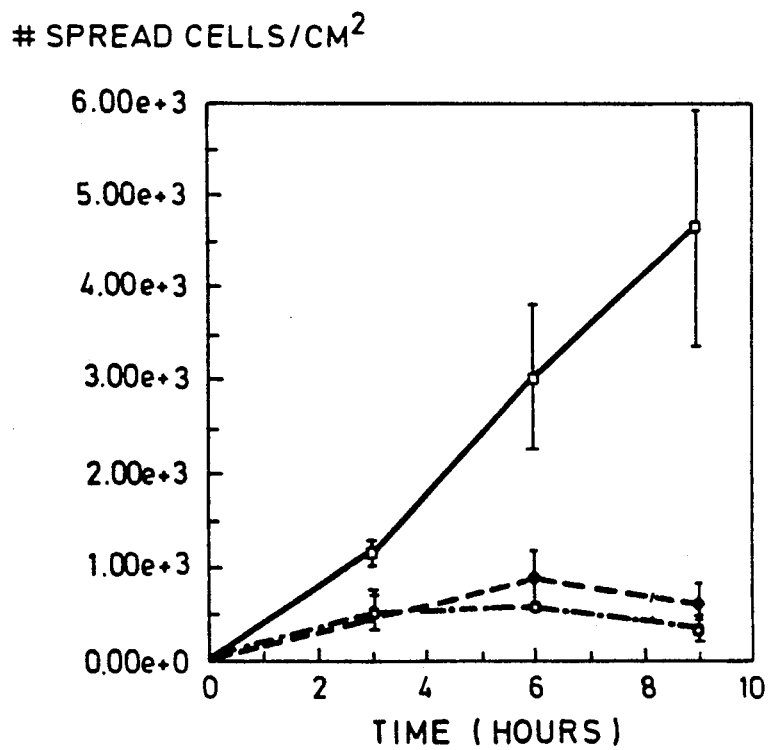
FIG. 5 shows a comparison of 3T3 spreading on GRGD coupled PET (solid curve, open boxes) versus GRGD adsorbed to PET (hatched curve, solid diamonds) and untreated PET (dot-hatched curve, open boxes).
Figure 6:
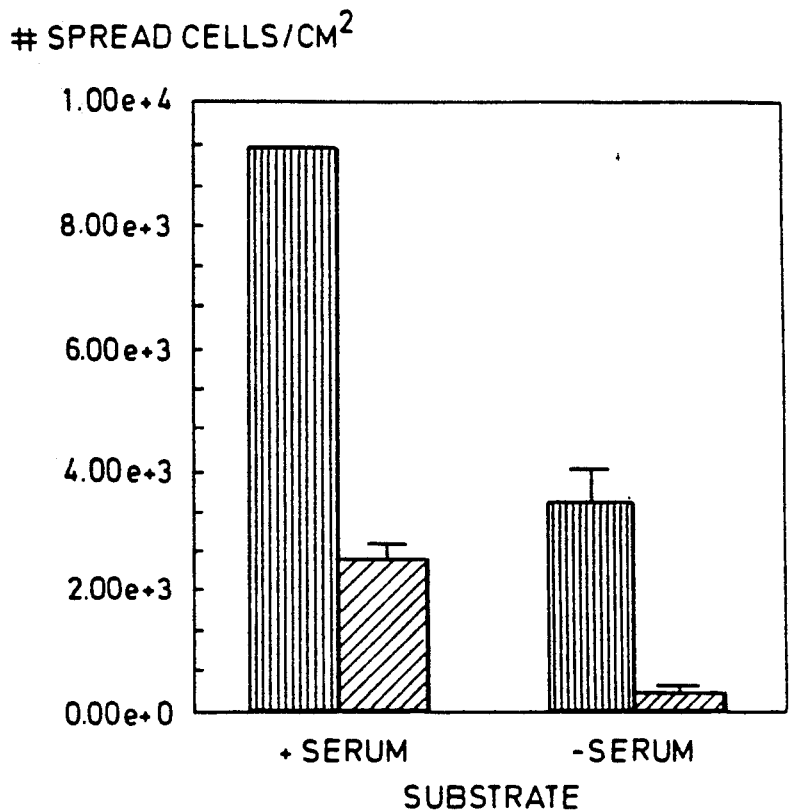
FIG. 6 shows the amount of 3T3 spreading on the modified (solid bars) and unmodified (hatched bars) films in a serum-free and complete medium. The extent of cell spreading was determined 2 hours after inoculation on each film. Cells were seeded at a density of 10,000 cells/cm$^2$.

Comparison of GRGD coupled PET films with pretreated untresylated films that were incubated with GRGD for the normal coupling time demonstrated that either little peptide adsorbed to the latter films or that the adsorbed peptide was not available for the receptor-mediated adhesion response (FIG. 5). The GRGD modified surfaces supported much better 3T3 cell adhesion than the untreated PET even in the presence of serum, which is indicative of an intrinsic activity on the modified surface (FIG. 6).

Figure 7:
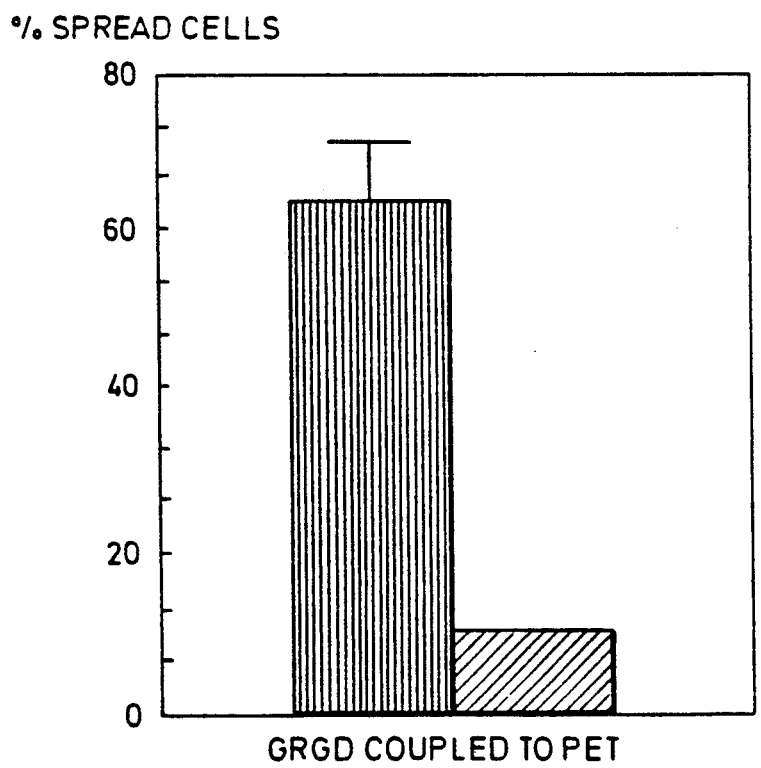
FIG. 7 shows the effects of soluble RGDS on spreading 3T3 cells on the GRGD derivatized PET films in serum-free culture medium. Cells were preincubated for 30 minutes with RGDS prior to inoculation of the films. The extent of cell attachment was determined 3 hours after inoculation. Cells preincubated with RGDS (hatched bar). Untreated control cells (solid bar).

The competition experiment resulted in a 75% reduction of attachment to the modified surfaces in the presence of about 90 ug/ml RGDS, which further demonstrates the biospecific activity of the substrates (FIG. 7). Gross morphology (FIG. 3) of spread 3T3 fibroblasts in serum-free medium on the modified films appeared normal (FIG. 3).

These results indicate that the complete adhesive response of this cell line and others is not obtained on RGDS modified surfaces. This is not a general phenomenon however, as some cell types including normal rat kidney fibroblasts and Nil 8, a normal hamster fibroblast cell line, have been shown to fully respond to substrates containing only RGD peptides (14). Growth on the GRGD derivatized-PET was serum dependent and was similar to that on unmodified PET (FIG. 8), but the initial attachment and spreading was more rapid, as indicated by the observation that the GRGD curve leads (open boxes) the control curve (solid diamonds) in this figure.

Attachment and spreading of porcine aortic endothelial cells on the GRGD coupled surfaces was also serum independent as expected, since vascular endothelial RGD directed receptors have been characterized (15). PAE cell spreading in complete medium was much more extensive on the GRGD derivatized films than the untreated films at four hours, but both surfaces had confluent monolayers of cells at twenty four hours. These observations indicate that the kinetics of PAE cell attachment was more rapid on the modified surface.

Applicants' disclosed methods provide a means for obtaining stable, chemically defined surfaces for use in studying cellular responses to insoluble extracellular matrix signals. It provides a means by which to decouple cell adhesion and spreading from protein adsorption. In this sense, it may be useful for those who prefer to use serum-free cell culture media (i.e., media in which purified proteins are added individually rather than introduced from serum) in that cell adhesion molecules (CAMs) do not need to be included. Whether these surfaces are capable of supporting cell growth at very low serum concentrations remains to be determined.

It should be understood that, in the presence of the media proteins, the GRGD surface is rapidly covered by adsorbed proteins. This is not problematic, however, as Applicants' studies with albumin in the culture media (FIGS. 4, 5, 7) indicated that the high affinity RGD-integrin association is capable of competing favorably with the adsorbed proteins. Cell detachment may be accomplished by calcium chelation, as the RGD-integrin affinity is calcium dependent.

It should also be noted that cell function is highly dependent upon the cell attachment surface (16, 17). This surface may provide a local environment that is closer to the one in vivo, and hence stimulate stronger adhesion and/or higher productivity.

Example 6—Peptide Derivatization of a Glass Surface

The present example was designed to outline the most preferred method of derivatizing a ceramic surface, such as glass, to provide a cell receptor-mediated adhesion-promoting substrate.

Glycophase glass was prepared by the method of Ohlson et al. (18). Glass coverslips (18 by 18 mm; Thomas) were soaked in 0.5 M sodium hydroxide for two hours, rinsed in deionized water, and immersed in an aqueous solution (1% pH 5.5) of (3-glycidoxy-propyl)trimethoxysilane (Petrarch Systems, Inc.). The preparation was heated and maintained at 90° C. for 2 hours. The pH was then adjusted to 3.0 followed by heating again for 1 hour to convert the oxirane moieties on the derivatized glass to glycol groups. Dry glycophase glass coverslips were rinsed with dry acetone (dried over molecular sieve 4A; Fisher). To about 1 ml of dry acetone, about 200 ul of dry pyridine and about 100 ul of dry tresyl chloride (Fluka) were added. A minimal volume of this mixture was added to the upper surface of each glycophase glass coverslip placed in a glass crystallization dish. The reaction was allowed to proceed for about 10 minutes at room temperature, then the coverslips were rinsed in about 1 mM hydrochloric acid and finally rinsed in an about 0.2 M sodium bicarbonate buffer at pH 9 (coupling buffer). Coupling buffer containing between about 5–30 ng/ml of peptide, preferably about 10 ng/ml, was added at a minimal volume on the coverslips and incubated for about 20 hours at room temperature to graft the peptide to the surface. The peptides used in this study were synthesized as outlined in Example 1. The peptide containing buffer was removed after an about 20 hour incubation period and replaced with coupling buffer containing an about 0.8 M beta-mercaptoethanol. The coverslips were incubated for about 2 hours so that unreacted tresyl groups would react with a nonadhesive moiety.

Measurement of Peptide surface concentration

GRGDY was radiolabeled by adding about 20 ug of peptide to phosphate buffered saline, pH 7.4, containing about 5.0 mCi of $Na^{125}I$ and incubating for about 15 minutes at room temperature with Iodobeads (Pierce) according to the manufacturer's instructions. The labeled peptide was purified by loading the reaction mixture on a Sep-Pak $C_{18}$ sample preparation cartridge (Waters) that was washed with methanol-$H_2O$-trifluoroacetic acid (TFA) (80:19:1 v/v) and reequilibrated with PBS. The cartridge was washed with 1% v/v TFA to eluate unincorporated iodine. The reaction mixture was fractioned using 10% stepwise increases in methanol concentration in 1% TFA with the methanol-$H_2O$-TFA (80:19:1 v/v) as the final eluant. The cartridge was washed with each concentration until the radioactivity returned to a baseline level. Each fraction was analyzed for peptide content by measuring absorbance at 220 nm (epsilon=8441 $M^{-1}$ $cm^{-1}$). Greater than 90% of the eluted peptide was in the methanol-$H_2O$-TFA (40:59:1 v/v) fraction, which was lyophilized and reconstituted in PBS. The specific activity of the peptide was then determined after counting a known amount of labeled peptide in an automatic gamma counter (Isoflex, ICN Micromedic Systems). The average specific activity was 44.0±2.0 mCi/mmol.

To determine peptide surface concentrations, radiolabeled peptide was added to coupling buffer (0.2M sodium bicarbonate, pH 10) at various concentrations, and incubated for 20 hours on tresyl activated glass at room temperature. Input concentrations were defined as the moles of soluble peptide available for reaction per unit area of glass surface. Surface concentrations were defined as the moles of peptide coupled per unit area of glass and were determined by counting washed glass samples in a gamma counter and calculating the values based on the specific activity of the labeled peptide.

The synthetic peptides Gly-Arg-Gly-Asp-Tyr (GRGDY) and Gly-Tyr-Ile-Gly-Ser-Arg-Tyr (GYIGSRY), which contain the ligands for two important classes of cell adhesion receptors, were covalently coupled to the non-adhesive modified glass surface, glycerol propylsilane bounded glass (glycophase glass) by the N-terminal Gly. Glycophase glass contains a covalently bound organic layer that imbibes water and reduces protein adsorption similar to hydrogels without the associated problems of swelling and bulk permeation of aqueous solutions. Since glycophase glass absorbs proteins poorly, it alone is not suitable for supporting cell adhesion, even with serum in the medium. Therefore, GRGDY and GYIGSRY were coupled to glycophase glass using the tresyl chloride immobilization method of Nilsson, et al. (1987), *Methods Enzymol.*, 135:65–78). The Nilsson, et al. article is specifically incorporated herein by reference.

The N-terminal "G" was used as a spacer between the adhesive peptide and the surface, and the C-terminal "Y" was used for radioiodination. Since primary amines serve as nucleophiles that react and covalently bind to tresylchloride-activated supports, the peptides employed linked to the glycophase glass exclusively through the primary amine of the N-terminal "G". The surface concentration of peptide was measured by $^{125}I$ radiolabeling and was 12.1 picomoles/cm$^2$. This derivatization method produces chemically stable substrates, which may be useful in studying receptor-mediated cell adhesion, as the quantity of peptide available at the surface may be precisely measured and controlled.

Example 7—Adhesion and Spreading of Cells on a Peptide Derivatized Glass Surface The present examples was designed to determine the effectiveness of the proposed chemical glass surface treatments in promoting the amount and rate of cell adhesion to a glass surface.

Substrate Preparation

Glycophase glass substrates were prepared by the method described in Example 6. These modified substrates supported the adhesion and spreading of cultured human foreskin fibroblasts (HFFs) independently of adsorbed proteins.

Parameters Measured

The biological activity of both grafted GRGDY and GYIGSRY was assessed by measuring the adhesion and spreading of HFF in the presence and absence of serum in the medium. Focal contact formation and cytoskeletal organization were also observed on these substrates.

Results

HFF spreading rates were much slower on grafted YIGSR (GYIGSRY) peptide substrates than on the RGD-containing (GRGDY) peptide surfaces. Cells formed focal contacts or absence on the RGD-derivatized substrates in the presence of serum. Focal contacts formed on &:he YIGSR-grafted surfaces only when serum was present in the medium and had morphologies distinct from those observed on the RGD-containing surfaces (FIG. 10; FIG. 12).

Serum influenced microfilament organization and the extent of spreading of adherent cells, although adsorption of adhesion proteins was minimal on all surfaces.

Example 8—Comparative Studies of Peptide Fragments GRDGY, GYGSRY and GRGEY on a Derivatized Glass Surface Derivatized glass surfaces were prepared according to the method described in Example 6 employing the GRGDY, GRGEY and GYGSRY peptides. HFF cells were then platted onto each of the prepared surfaces. Spreading and growth rate determinations were then made. Untreated glycophase glass was found to support no cell adhesion, even when cells were incubated on this substrate in serum-supplemented medium, which is indicative of a low protein-binding substrate (Table 1).

Beta-mercaptoethanol-grafted glass was equally non-supportive of cell adhesion and spreading, as indicated in the results of the cell spreading studies (FIGS. 2B, D,; 3 B, D). Since beta-mercaptoethanol was employed to react with any remaining tresyl groups on the surface of the glass, a non-adhesive background was established on this surface. Furthermore, grafted GRGEY, which does not intrinsically support receptor-mediated cell adhesion and adsorbs proteins similarly to grafted GRGDY, did not support cell adhesion (Table 1). This result suggests that immobilizing GRGDY on glycophase glass does not significantly enhance protein adsorption on this substrate.

Spreading and Growth Rate Determination

HFF cells were prepared as outlined in Example 4. These cells were harvested for experiments and rinsed twice with $Ca^{2+}$- and $Mg^{2+}$-free phosphate buffered saline (PBS) and then incubated in 0.05% trypsin plus 0.53 mM EDTA in PBS (GIBCO) for 10 minutes. Cells were collected by centrifugation and resuspended in serum-supplemented medium or serum-free medium which consisted of DMEM with 2 mg/ml of heat-inactivated (90° C., 10 min.) albumin (Sigma) and antibiotics.

Cells suspended in complete or serum-free medium were seeded on the substrates at a density, of about 10,000 cells/cm$^2$ and allowed to attach and spread at 37° C. in 5% $CO_2$. An inverted microscope (Fluovert, Leitz) equipped with a phase contrast objectives and a high resolution video camera (67M series, Dage-MTI) were used to visualize spreading cells at various time points.

Images were digitized with an image processing system (Series 150, Imaging Technology Inc.) and the areas of individual cells were determined by tracing the perimeter of each cell in the digitized images with a tracing pad (Digi-Pad, GTCC) and computing the area enclosed by each trace with an integration routine. At least 100 cells were analyzed and cumulative histograms were constructed for each time period so that cell spreading rates could be determined.

Cell growth in complete medium on substrates was assayed by visualizing cells with 100× phase contrast microscopy. At various time points, cells were counted in ten fields and the number of cells power unit area of growth surface was calculated based on an averaged cell count per area of field.

In the end point cell spreading assays protein synthesis was inhibited by treating cells with 20 ug/ml of cycloheximide for about 30 minutes prior to inoculating them on substrates. The cells were maintained in medium containing cycloheximide throughout the experiment. Cells that were treated with soluble peptide were preincubated with medium containing peptide for about 30 minutes and were maintained in that medium throughout the experiment. Spread cells were scored in 10 fields according to methods described by Massia et al. (1989) (*Biochem. Engin. VI, Ann. N.Y. Acad. Sci.*, in press). The percentage of spread cells per field was calculated by multiplying the ratio of spread cells to the total number of cells per field by 100.

Morphological Studies

Cells adherent to peptide-grafted 24×50 coverslips (Thomas) were mounted in a culture chamber stage and fitted on the Fluorovent inverted microscope. A NPL Fluotar 100× (Leitz) objective was employed so that transmission phase contrast, and interference reflection (IRM) microscopy could be performed on the same field without changing objectives. Phase contrast and IRM images were acquired from live cells immersed in medium and maintained at 37° C. Illumination for phase contrast was provided by a 100 W halogen lamp and a model 050260 power supply (Leitz) equipped with a heat-reflecting filter. A 100 W mercury arc lamp powered by a HBO 100 model 990023 DC source (Leitz) was used for IRM. Images were acquired with a high resolution video camera (70 series, Dage-MTI) and digitized with the Series 150 image processing system. Digitized images were photographed from a high resolution video monitor (model PVM 1271Q, Sony) using Illford Pan F film.

Fluoresence Microscopy

Cells on peptide-grafted glass coverslips at the end of incubation times were rinsed in PBS and fixed for about 20 minutes with 3.7% (v/v) formaldehyde in PBS. They were then rinsed in PBS and permeabilized by incubation at room temperature for about 1 minute in PBS containing about 0.2% (v/v) TRITON X-100. Cells were then rinsed in PBS and stained for F-actin with a 20 minute incubation at room temperature with about 900 ng/ml rhodamine-conjugated phalloidin (Molecular Probes, Inc.). The coverslips were rinsed thoroughly with PBS and mounted on microscope slides in 50% PBS-50% glycerol These preparations were viewed and photographed on the Fluovert microscope equipped with a 100× PL Fluotar objective (Leitz).

RESULTS

Determination of GRGDY Surface Concentration

Figure 9:
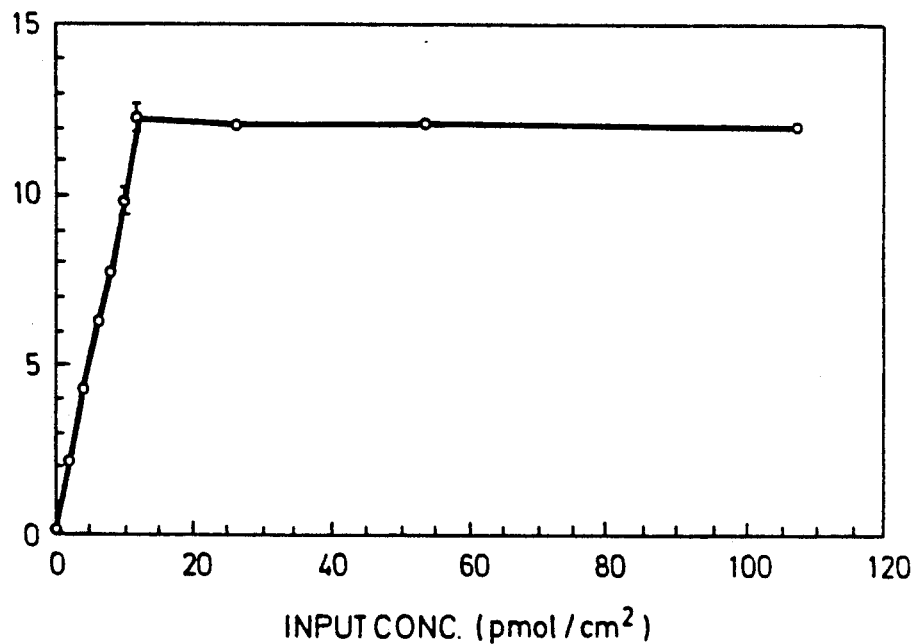
FIG. 9 shows surface concentration of GRGDY-$^{125}$I grafted to glycophase glass was added to coupling buffer (0.2M sodium bicarbonate pH 10) and incubated on tresyl activated glass at room temperature. Input concentrations were soluble peptide available for reaction per unit area of glass surface. Surface concentration is defined as the moles of peptide coupled per unit area of glass and were washed glass samples in a gamma counter and calculating the values based of the labeled peptide. Each point is the average of triplicate determinations surface concentration was 12.1 pmol/cm$^2$.

The number of reactive sites and the corresponding peptide concentration on the surface were determined by titration with the radiolabeled GRGDY (FIG. 9). Surface concentration of grafted GRGDY was determined to increase linearly with increasing concentrations of peptide available for coupling to the surface, reaching a maximum value of 12.1±0.1 picomoles/cm$^2$ (FIG. 9). Subsequent increases in input peptide concentrations above 12.0 picomoles/cm$^2$ did not further increase the surface concentration of the peptide. A maximum surface concentration of 12.1 picomoles/cm$^2$ corresponds to a surface coverage of 73,000 molecules per square micrometer, or a spacing of approximately 3.3 nm between peptides.

HFF Spreading Rates on Peptide-Grafted Substrates

Figure 10A:
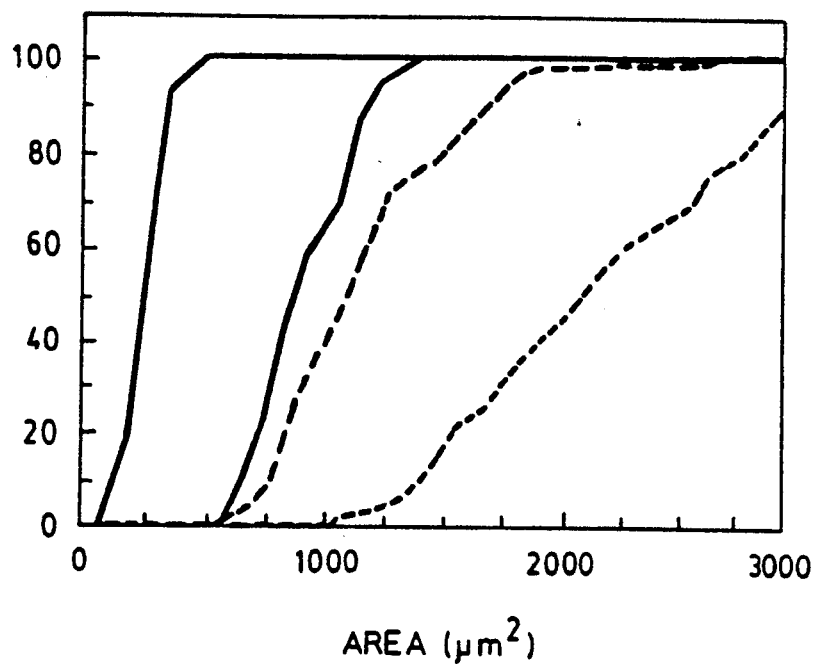
FIGS. 10A, 10B, 10C and 10D show cumulative histograms showing the cell areas of HFFs on glycophase glass with GRGDY. Cells were suspended in either complete medium (A) containing albumin (C), (D), and inoculated on the substrates. A and C represent data collected on the RGD-derivatized glass, whereas (B) and (D) represent nonadhesive control surfaces. The areas of individual cells were video microscopy coupled with digital image processing. Cell spreading observed on the peptide-grafted surfaces, even in the absence of serum; there was no cell spreading on the ungrafted surfaces even with serum, and most of these cells were nonadherent. At least 100 cells were analyzed at each time point to generate the cumulative data. Lines: (-) 15 minutes; (......) 30 min.; (-----) 60 min.; and (------) 120 min. Midpoint with 50% above and 50% below for the various time points (in order): A: 15 min. 265 um$^2$; 30 min. 906 um$^2$; 60 min., 1113 um$^2$; 120 min., 2130 um$^2$; B: 385,397, 448, 453; C: 248, 950, 864, 1207; D: 377, 325, 388, 388.
Figure 10B:
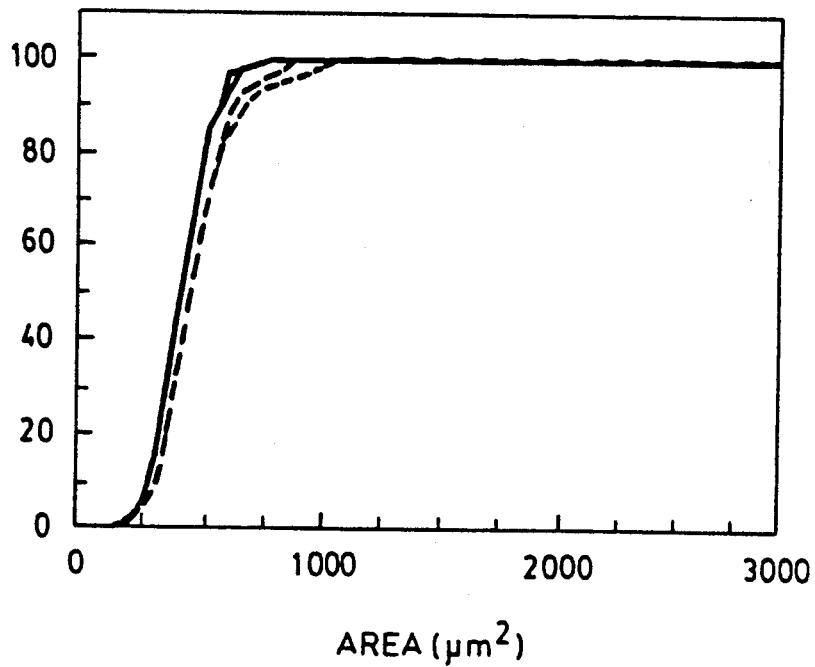
Figure 10C:
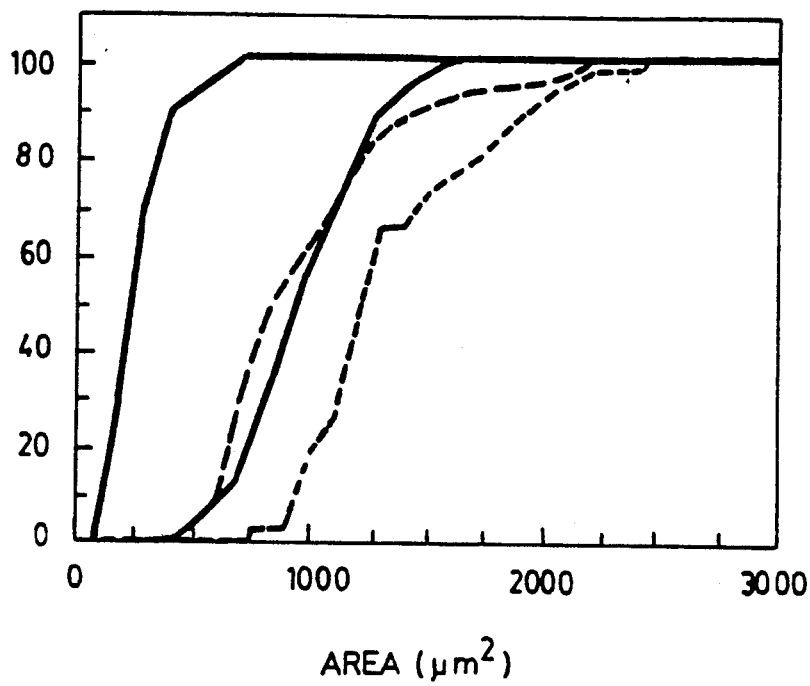
Figure 10D:
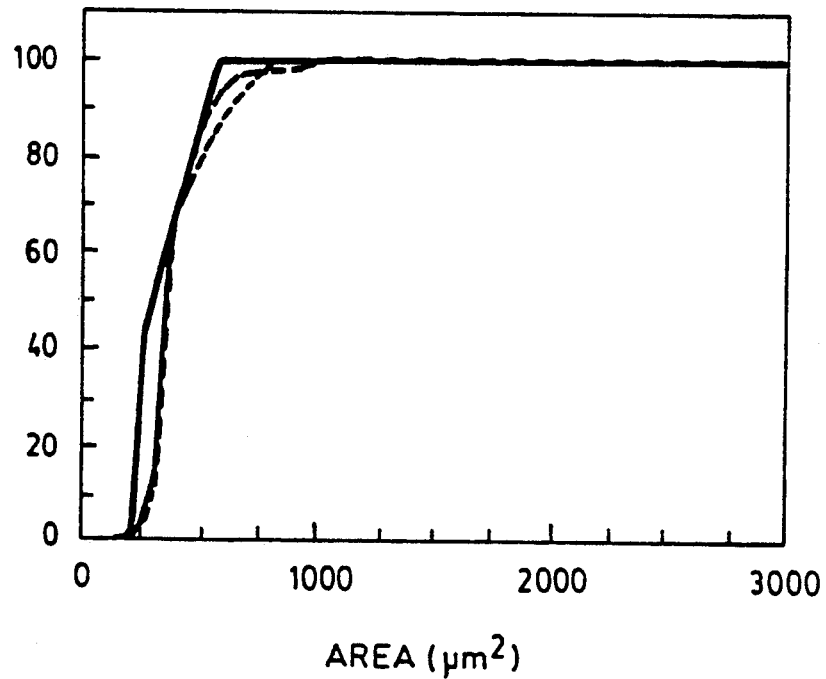

Cells were observed to spread progressively during the 2 hour period on the RGD-derivatized glass, both in the presence and absence of serum, with 50% of the cells analyzed having areas of 2130 um$^2$ or less 2 hours after seeding in complete medium (FIG. 10A), and 50% of the cells having areas 1210 um$^2$ or less 2 hours after seeding in serum-free medium (FIG. 10C). The average area of a well-spread cell on tissue culture plastic in complete medium was observed to be 2100 um$^2$, whereas a non-spread cell had an average area of 355 um$^2$. The area ranges of cells cultured on the nonadhesive surfaces did not vary over time in the presence or absence of serum, with 50% of the cells having areas less than 500 um$^2$ (FIGS. 10B, D). These results indicate that no spreading occurred on these surfaces, and most of the cells were observed to be nonadherent.

Cell spreading was also observed on YIGSR-derivatizing glass in the presence and absence of serum. Spreading rates were much slower on grafted YIGSR substrates than on the RGD-containing surfaces, requiring more than 6 hours for complete spreading in complete (FIG. 10A) or serum-free (FIG. 10B) medium. After about 9 hours in serum-free medium, 50% of the cells analyzed had areas 1400 um$^2$ or less (FIG. 10B), which is comparable to areas of well-spread HFFs on the RGD surfaces in serum-free medium. Serum was observed to enhance cell spreading on the YIGSR surfaces; 50% of the cells analyzed had areas of 2333 um$^2$ or less (FIG. 10A) 9 hours after inoculation. Nonadhesive control surfaces were identical to the ones prepared for the RGD-derivatized glass studies and cell spreading was not observed on these surfaces; 50% of the cell areas never exceeded 600 um$^2$ throughout the time frame of the study (FIGS. 10C, D).

Effects of Grafted GRGDY on Cell Growth

Figure 11:
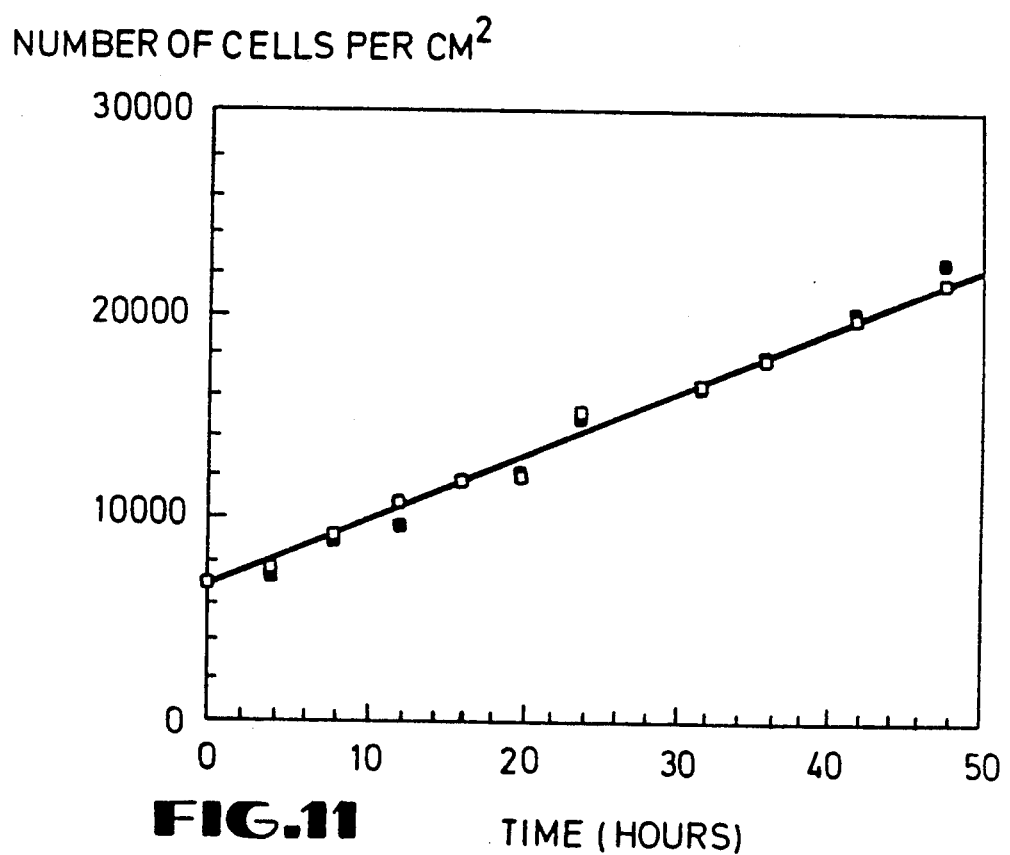
FIG. 11 shows growth of HFFs on GRGDY-derivatized glycophase glass (open squares) and untreated borosilicate glass (solid squares) in DMEM supplemented with 10% fetal calf serum. Cells were visualized with 100× phase contrast microscopy. The number of cells per unit area of growth surface was calculated based on an averaged cell count per area of field from a sample size of 10 fields per time point. The similar growth rates indicate that cells are able to round-up from the peptide-grafted surfaces and to subsequently divide.
Figure 12A:
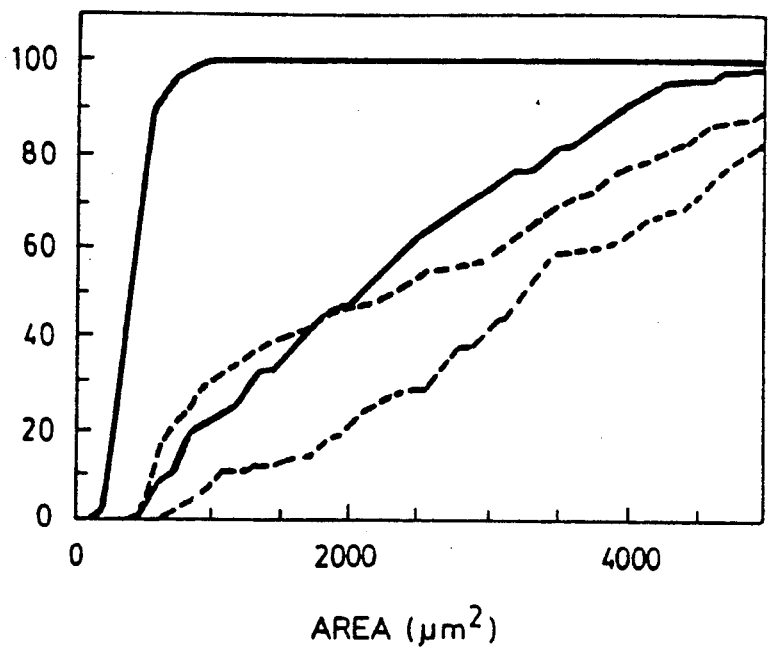
FIGS. 12A, 12B, 12C and 12D show cumulative histograms showing the cell areas of HFFs on glycophase glass derivatized with GYIGSRY. Cells were suspended in either complete medium (A), (B), or serum-free medium containing albumin (C), (D), and inoculated on the substrates. (A) and (C) represent data collected on the YIGSR-derivatized glass, whereas (B) and (D) represent data collected on the nonadhesive control surfaces. The areas of individual cells were determined by phase contrast video microscopy coupled with digital image processing (12). Cell spreading was observed on the peptide-grafted surfaces, even in the absence of serum; there was no cell spreading on the ungrafted surfaces even with serum, and most of these cells were nonadherent. (At least 100 cells were analyzed at each time point to generate the cumulative data.) Lines: (solid line) 0 hours; (dotted line) 3 hours; (heavy dashed) 6 hours; and (light dashed) 9 hours). Midpoint cell area, with 50% of the cells above and 50% below for the various time points (in order): A: 0 hours; 505 um$^2$; 3 hours, 2200 um$^2$; 6 hours, 2333 um$^2$; 9 hours, 3375 um$^2$; B: 340, 520, 486, 517; C: 517, 1045, 1033, 1400; D: 245, 306, 362, 514.
Figure 12B:
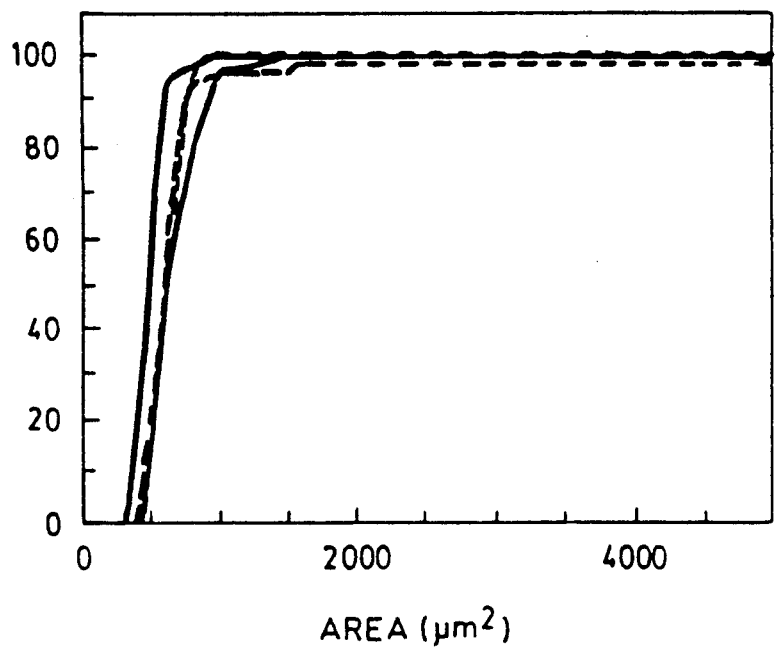
Figure 12C:
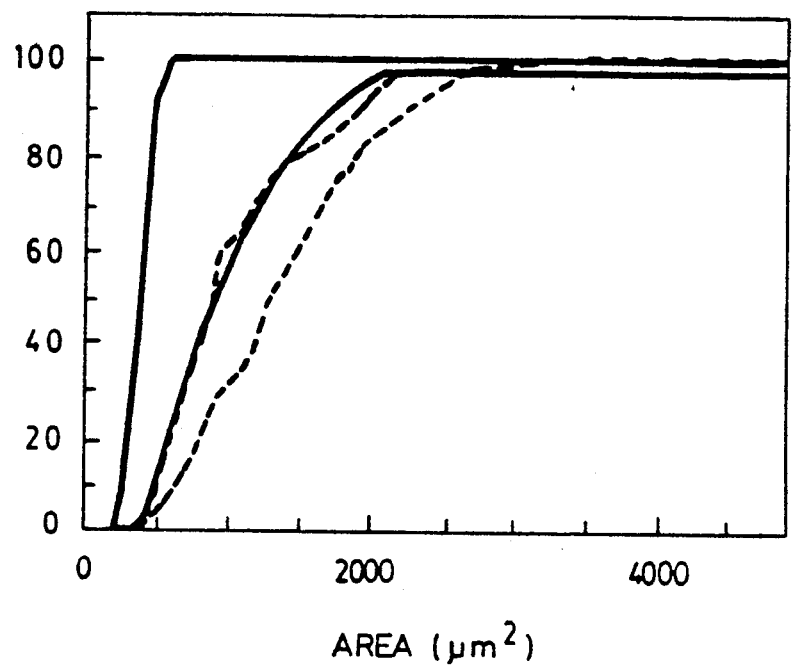
Figure 12D:
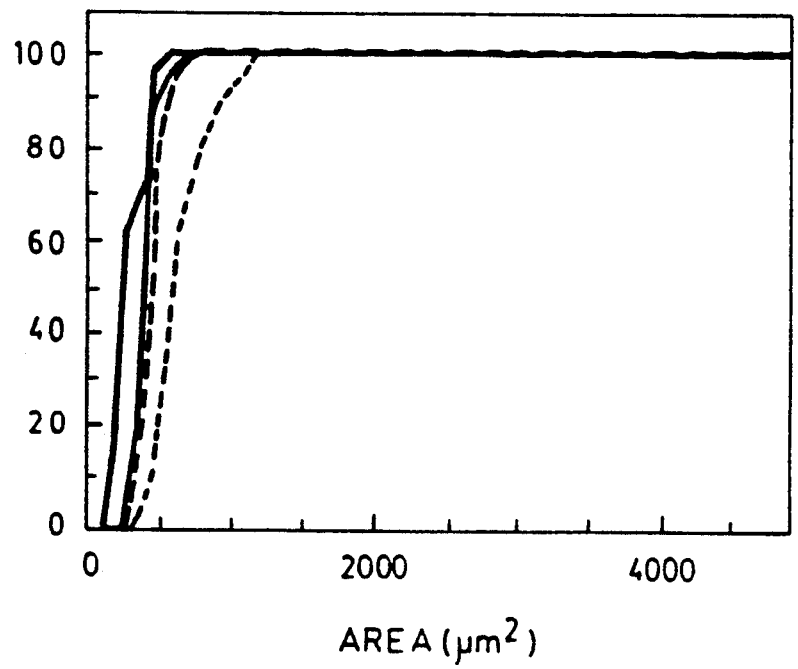

The effect of these RGD-containing substrates on cell growth was checked by monitoring growth of HFFs seeded on glass containing coupled GRGDY. No difference in growth rate was observed when we compared growth of cells cultured on RGD-derivatized glass with that of untreated (not glycophase) glass (FIG. 11).

Characterization of Cellular Responses to the Peptide-Grafted Substrates

Since serum enhanced cell spreading on the peptide-containing glass, it was postulated that the peptides grafted to the surface of the nonadhesive glass promoted the adsorption of serum and excreted cellular proteins which would augment cell adhesion and spreading on these substrates. To check this possible effect, the synthetic peptide GRGEY was coupled to glass, and cell spreading on these surfaces was assayed. The substitution of glutamic acid (E) for aspartic acid (D) (an addition of one methylene group to the carboxylic acid side chain) has been demonstrated to abolish the adhesion-promoting activity of the peptide (8) but should have little impact on the way the peptide interacts with potentially adsorbing proteins.

No cell spreading was observed on covalently bound GRGEY after about 8 hours, even when complete medium was used and cellular protein synthesis was not inhibited (Table 1). These findings suggest that the covalently-bound GRGEY peptides do not significantly increase the adsorption of cell adhesion proteins which would promote and enhance cell spreading. This is to say that, the cell adhesive behavior of the peptide grafted surfaces was due to the peptide's affinity for cell-surface receptors and not due to enhanced serum protein adsorption by the peptide.

To determine if protein synthesis played a role in cell spreading on the RGD and YIGSR-linked substrates, and if serum significantly increased the fraction of cells that spread at a time point where spreading was complete, the percentage of spread cells was determined on each surface under different conditions after an 8 hour incubation period. It was observed that neither protein synthesis nor the presence of serum in the medium affected the fraction of cells spread on the RGD-and YIGSR-derivatized glass (Table 1). Cell spreading on both the peptide-grafted surfaces was completely inhibited, however by the presence of soluble peptide in the medium (Table 1), indicating that cellular adhesion on these substrates is governed primarily by cell receptor-ligand interactions.

TABLE 1

| Peptide grafted to surface | Serum in medium (10% v/v) | Cyclo-heximide in medium (20 ug/ml) | Peptide in medium (200 ug/ml) | Spread cells (%) |
|---|---|---|---|---|
| GRGEY | + | + | − | 0 |
| | + | − | − | 0 |
| | − | + | − | 0 |
| | − | − | − | 0 |
| GRGDY | + | − | − | 87 ± 8 |
| | + | + | − | 80 ± 9 |
| | − | − | − | 91 ± 4 |
| | − | + | − | 83 ± 10 |
| | − | − | +(RGDS) | 0 |
| | − | + | +(RGDS) | 0 |
| GYIGSRY | + | − | − | 78 ± 7 |
| | + | + | − | 82 ± 2 |
| | − | − | − | 81 ± 12 |
| | − | + | − | 90 ± 2 |
| | − | − | +(YIGSRY) | 0 |
| | − | + | +(YIGSRY) | 0 |

Cell-Substrate Contacts and Cytoskeletal Organization

Cells were examined live by IRM and phase contrast microscopy at about 4 hours after seeding on RGD-derivatized substrates and about 8 hours after seeding on YIGSR-derivatized substrates. Fixed specimens were stained with rhodamine-conjugated phalloidin to evaluate microfilament distribution in spread cells. All images were digitized and a high pass filter was employed to enhance detail.

Figure 13A:
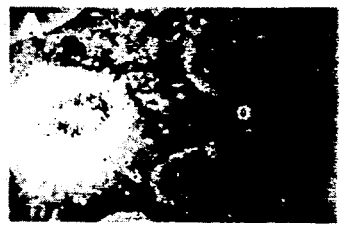
FIGS. 13A, 13B, 13C and 13D show phase contrast (13 A, C) and IRM (13 B, D) micrographs of spread HFFs on RGD-grafted glass. Cells were incubated for 4 hours in serum-free (13 A, B) or complete medium (13 C, D). Scale bar=10 um.
Figure 13B:
Figure 13C:
Figure 13D:
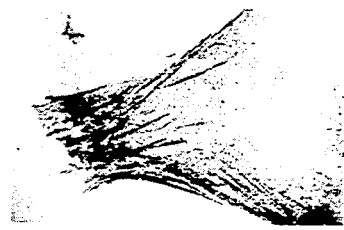
Figure 14A:
FIGS. 14A, 14B, 14C and 14D show phase contrast (14 A, C) and IRM (14 B, D) micrographs of spread HFFs on YIGSR-grafted glass. Cells were incubated for 8 hours in serum-free (14 A, B) or complete medium (14 C, D). Scale bar=10 um.
Figure 14B:
Figure 14C:
Figure 14D:

Cells seeded in the absence of serum on RGD-grafted glass, formed small, round focal contacts that were observed mainly on the outer margins of cells (FIG. 13B). Serum supplemented medium supported formation of large elongated focal contacts typical of cells that spread on cell adhesion molecule-coated substrates (FIG. 13D). Cells spreading on YIGSR-grafted glass did not form focal contacts in the absence of serum (FIG. 14B). Focal contacts were well-defined on this substrate when medium was supplemented with serum (FIG. 14D), however they were morphologically distinct from those of FIG. 13D on the RGD-derivatized substrates. Focal contacts on the YIGSR-derivatized substrates were elongated, similar to those in FIG. 13D, but were predominantly located in the outer margins of cells. Phase contrast images (FIGS. 13A, C; 14A, C) did not reveal any obvious morphological differences between spread cells on the various substrates, but serve as a corresponding image for the IRM images.

Figure 15A:
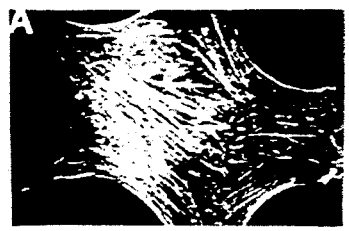
FIGS. 15A, 15B, 15C and 15D show fluorescent micrographs of HFFs stained for F-actin. HFFs were incubated for 4 hours on RGD-derivatized substrates in serum-free (15 A) and complete (15 B) medium. 15 C and 15 D are spread cells on YIGSR-derivatized substrated after an 8 hour incubation in serum-free (C) and complete (D) medium. Scale bar=10 um.
Figure 15B:
Figure 15C:
Figure 15D:
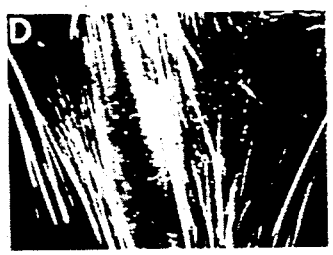

Rhodamine-phalloidin staining revealed an extensive network of acting microfilament bundles in spread cells on RGD-grafted glass, that were incubated in serum-free (FIG. 15A) or complete (FIG. 15B) medium. Bundles formed by spreading cells incubated in serum supplemented medium stained more intensely than those formed by cells incubated in serum-free medium, which indicates that thicker fibers formed when serum was present. Cells incubated in serum-free medium on the YIGSR-grafted substrates formed very few microfilament bundles (FIG. 15C), however thick bundles formed when serum was present in the medium (FIG. 15D).

These studies show that adhesion-promoting synthetic peptides of minimal sequences can be covalently grafted to the surface of a nonpermeable, nonadhesive material such as glycophase glass to produce biologically active, chemically well-defined surfaces that support cell adhesion. These substrates may be useful in the study of cell adhesion, as the amount of peptide available on the surface may be precisely measured (FIG. 9) and it is possible to control the amount of peptide grafted competitively by adding controlled amounts of a nonadhesive species, such as glycine, in the coupling buffer. This could be an important requirement for model substrates of receptor-mediated cell adhesion, since it has been recently shown that integrin-mediated cell adhesion to adsorbed RGD-albumin conjugates is very sensitive to the density of RGD-containing groups that are covalently attached to the native protein.

Example 9—Stability of Peptide-Grafted Substrates

Radiolabeled GRGDY peptides were covalently grafted to glycophase glass substrates in order to determine how stable the immobilized peptides were to heat and proteolysis. The percent (%) loss in radioactivity was interpreted to indicate the percent (%) of immobilized peptide that was degraded and thus unavailable for enhancing cell adhesion.

The data suggests that these peptide-grafted substrates are quite stable to autoclaving (steam sterilization at 121° C.), since no loss of radioactivity was evident after this treatment (Table 2). Also, no radioactivity was lost after culturing cells on these substrates for 1 week. The data also indicates that the treated substrates are stable to cellular proteases.

TABLE 2

Stability of RGD-derivatized Glycophase Glass

| Environmental Stress to the Substrate | % loss of radioactivity |
|---|---|
| Autoclave (121° C., 15 min) | 0 + 0 |
| Cell Culture (1 week) | 2 + 1 |
| Exposure to Trypsin | 5 + 4 |

Figure 17:
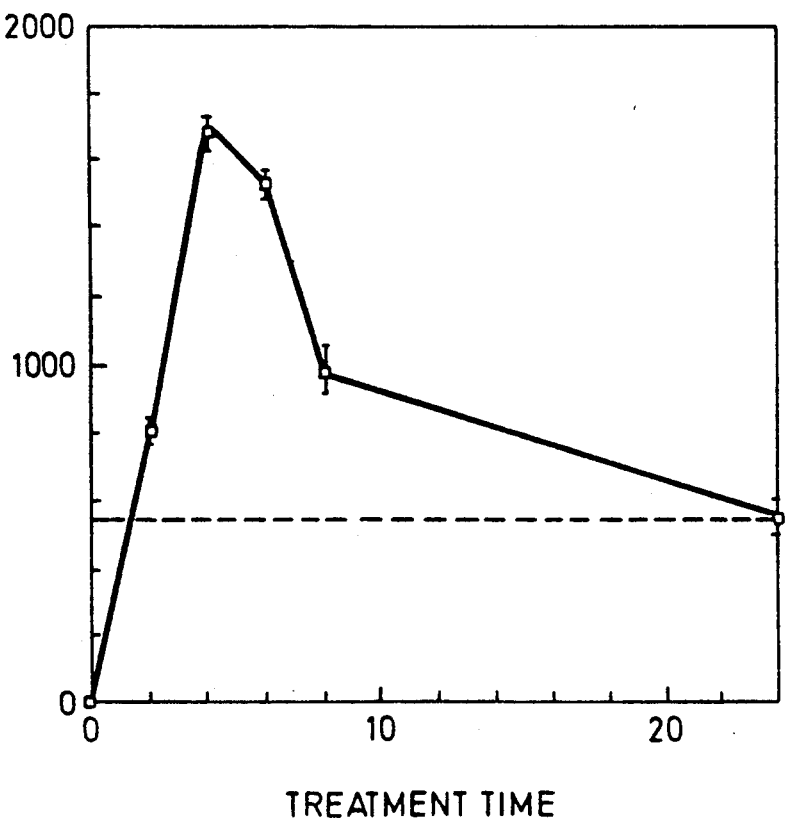
FIG. 17 shows the rate of cell spreading observed on peptide derivatized PET (polymer) surfaces versus nontreated PET (polymer) surfaces.

Example 10—Peptide Adsorption Comparison of GRGD Coupled PET Substrates With Pretreated Untresylated PET Substrates The GRGD derivatized PET substrates were characterized by their ability to support active adhesion of cells on their surfaces. The PET pretreatment was optimized by coupling GRGD to tresyl chloride activated films that were hydroxylated for various time periods. Cell spreading assays using NIH/3T3 fibroblasts were performed to determine conditions that supported a maximal response. An about four hour pretreatment appeared to be optimal for maximum cell adhesion and spreading (FIG. 17).

Comparison of GRGD coupled PET films with pretreated untresylated films that were incubated with GRGD for the "normal" coupling time (about 20 hours) demonstrated that either little peptide adsorbed to the film or that the adsorbed peptide was not available for the receptor mediated adhesion response (FIG. 5). The GRGD modified surfaces supported much better 3T3 cell adhesion than the untreated PET, even in the presence of serum, which is indicative of an intrinsic activity on the modified surface (FIG. 6). The competition experiment resulted in a 75% reduction of attachment to the modified surfaces in the presence of about 90 ug/ml RGDS, which further demonstrates the biospecific activity of the substrates (FIG. 7).

Figure 8:
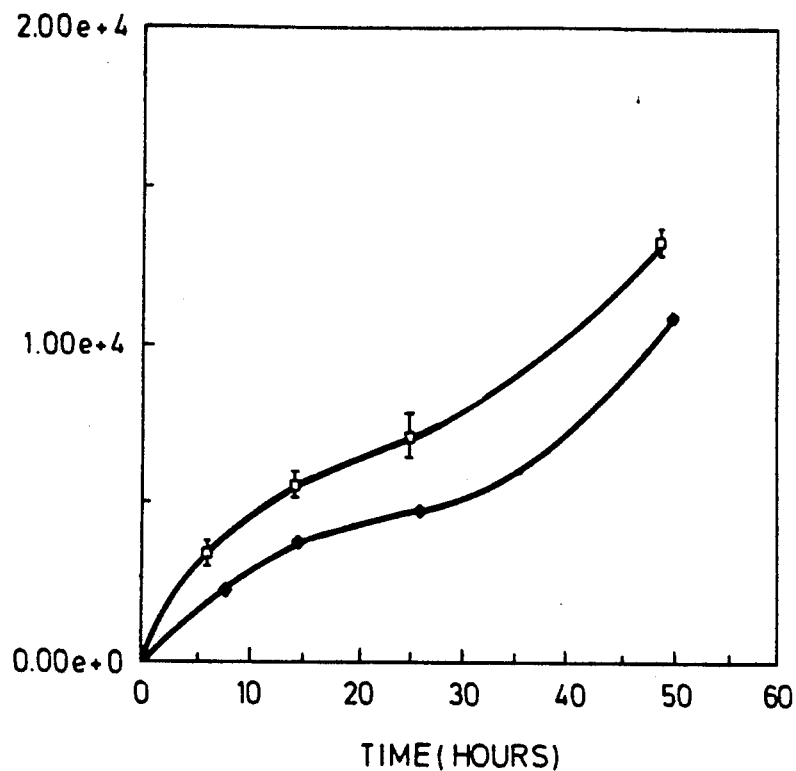
FIG. 8 shows the growth kinetics of 3T3 cells on GRGD derivatized (open squares) and untreated (solid diamonds) PET surfaces. These studies were performed in complete medium.

Gross morphology (FIG. 3) of spread 3T3 fibroblasts in serum-free medium on the modified films appeared normal, however, microfilament bundle and stress fiber formation could not be detected under these conditions. These results indicate, as others have shown with absorbed RGD peptides (19, 20, 14), that the complete adhesive response of this cell line and others is not obtained on these modified surfaces. This is not a general phenomenon however, as some cell types including normal rat kidney fibroblasts and Nil 8, a normal hamster fibroblast cell line, have been shown to fully respond to substrates containing only RGD peptides (14). Growth on the GRGD derivatized PET was serum dependent and was similar to that on unmodified PET (FIG. 8), but the initial attachment and spreading was more rapid, as indicated by the observation that the GRGD curve leads the control curve (FIG. 8).

Figure 16:
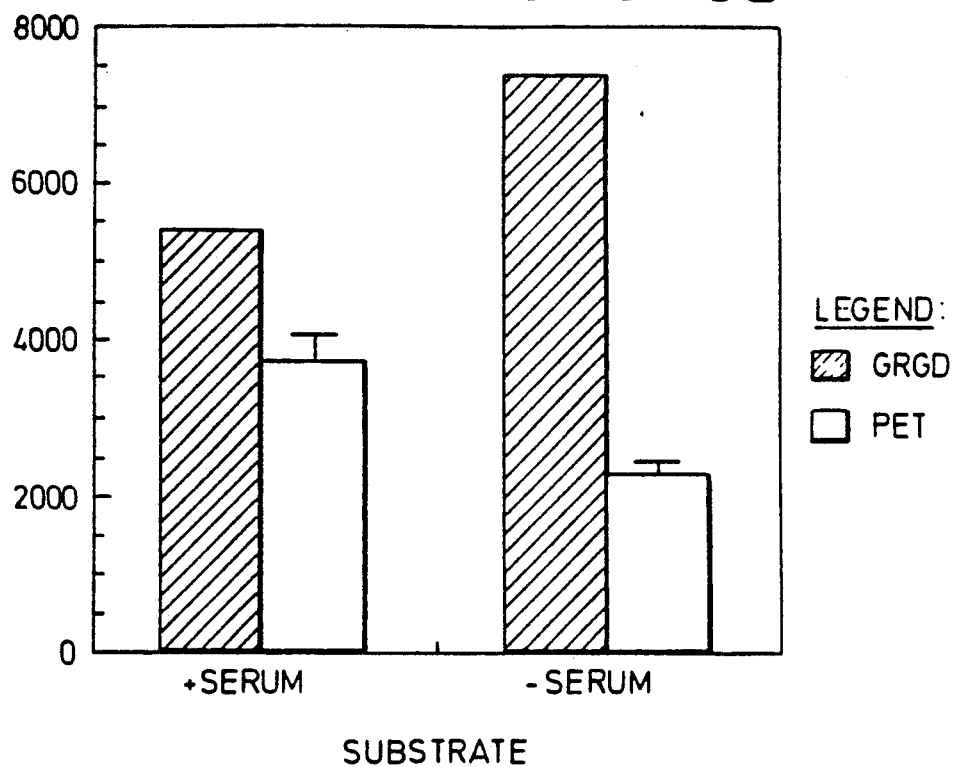
FIG. 16 shows the effect of the absence or presence of serum on porcine aortic endothelial cell spreading in cell cultures established on either PET or GRGD peptide derivatized PET surfaces.

Attachment and spreading of porcine aortic endothelial cells on the GRGD coupled surfaces was also serum independent (FIG. 16). As expected, since vascular endothelial RGD directed receptors have been characterized (15). PAE cell spreading in complete medium was much more extensive on the GRGD derivatized films than the untreated films at four hours, but both surfaces had confluent monolayers of cells at twenty-four hours. These observations indicate that the kinetics of PAE cell attachment was more rapid on the modified surface.

Example 11—An Indwelling Catheter with a Bioadhesive Dacron Velour Cuff in a Rabbit (Prophetic)

A dacron velour cuff with an inner diameter of about 1 mm and an outer diameter of about 3 mm would be placed around a polyethylene catheter at the base and glued in place with surgical-grade cement. Prior to placement a cuff would be treated in the acetic acid/formaldehyde solution as described in Example 3 to hydroxylate the surface. The tetrapeptide GRGD would then be covalently attached to the cuff material surface as described in Example 3 by tresyl activation and coupling. The fur of the animal would be shaved along the abdomen, and the skin opened with a lateral cut of about 1 cm length. The catheter would be inserted into a vein, e.g. the descending vena cava, and the cuff would be placed just beneath the skin. The skin would be sutured together around the protruding catheter, such that it covered the cuff. The rates of bacterial infection on the catheter would then be measured. Several of the cuffs would be removed after a period of time, for example, 1, 2, 3 and 4 weeks for histological examination of tissue integration, regrowth, and inflammation. Control experiments would utilize unmodified dacron cuffs.

Example 12—A Nerve Regrowth Guide (Prophetic)

A polymer tube with a high permeability to water and oxygen with an inner diameter of about 1.5 mm and an outer diameter of about 3 mm would be used as a nerve regrowth guide in the rat. An example of a useful material would be poly(hydroxylethyl methacrylate). The lumen of the tube would be activated and coupled with the peptide GRGD or GYIGSR as described in Example 3. A nerve bundle in one leg would be severed and a section approximately 1 cm long would be removed. Both ends of the nerve bundles would be inserted into the ends of the tubular regrowth guide, and the edges of the guide would be tightly sutured to the epiaxonal tissue. The wound would be closed, and reinnervation would be measured electrophysiologically weekly. Control experiments would utilize unmodified poly(hydroxyethyl methacrylate) tubes.

The following references are cited throughout the Specification, and are hereby specifically incorporated in pertinant part by reference herein.

BIBLIOGRAPHY

1. Grinnell, F. (1978), "Cellular Adhesiveness and Extracellular Substrata", *International Review of Cytology*, 53: 67-149.
2. Couchman, et al., (1982), *J. Cell Biol.*, 93: 402-410.
3. Pearlstein, E., (1976), *Nature*, 262: 497-500.
4. Kleinman, et al., (1976), *Biochem. Biophys. Res. Commun.*, 72: 426-432
5. Grinnel, F. (1976), *Exp. Cell Res.*, 97: 265-274.
6. Grinnell, F. (1976), *Exp. Cell Res.*, 102: 51-62.
7. Hynes, et al., (1982), *J. Cell. Biol.*, 95: 369-377.
8. Pierschbacher, et al., (1984), *Nature*, 309: 30-33.
9. Pytela, et al., (1985), *Cell*, 40: 191-198.
10. Pytela, et al., (1985), *Proc. Natl. Acad. Sci. U.S.A.*, 82: 5766-5770.
11. Fitzgerald, et al., (1985), *J. Biol. Chem.*, 260: 11366-11374.
12. Ruoslahti, et al., (1987), *Science*, 238: 491-497.
13. Hynes, R. O., (1987), *Cell*, 48: 549-554.
14. Singer, et al., (1987), *J. Cell. Biol.*, 104: 573-584.
15. Cheresh, A. (1987), *Proc. Natl. Acad. Sci. U.S.A.*, 84: 6471-6575.
16. Variani, et al., (1986), *In Vivo*, 22: 575-582.
17. Aubert, et al., (1987), *J. Biomed. Mater Res.*, 21: 585-602.
18. Ohlson, et al., (1978) *FEBS Letters*, 93, 5-9.
19. Woods, et al., (1986), *EMBO J.*, 5: 665-670.
20. Streeter, et al., (1987), *J. Cell. Biol.*, 105: 507-515.
21. Paul, et al., (1976), *J. Appl. Pol. Sci.*, 20: 609-625.
22. Humphries, et al., (1986), *J. Cell Biol.*, 103: 2637-2647.

23. Mohr and Pommerening, (1985), *Affinity Chromatography: practical and theoretical aspects*, Chapter 4.
24. Costello and McCarthy (1987), *Macromolecules*, 20: 2819-2828.

What is claimed is:

1. A cell culture substrate of less than about 45% water comprising a surface with the terminal amine of a peptide covalently linked thereto, wherein said peptide is at least one of

| GRGD; | GRGDY; | GREDVY; or |
| GRGDF; | GYIGSR; | GREDV, |
| GRGDS; | GYIGSRY; | | and wherein the surface concentration of said peptide is less than about 50 pmol/cm$^2$, said substrate being capable of supporting cell focal adhesion formation and cell spreading.

2. The cell culture substrate of claim 1, wherein said peptide comprises 4 to 6 amino acid residues.

3. The cell culture substrate of claim 1 wherein the peptide is GRGD, GRGDY or GYIGSRY.

4. The cell culture substrate of claim 1 wherein the peptide is GRGD, GRGDY, or GYIGSRY and is covalently attached to said cell culture substrate at the N-terminal glycine of the peptide.

5. The cell culture substrate of claim 1, wherein said peptide is GRGD, GRGDF, GYIGSR, GYIGSRY GREDV or GREDVY.

6. The cell culture substrate of claim 1 or 5, wherein the peptide is GRGD.

7. The cell culture substrate of claim 1 or 5 wherein the peptide is GYIGSR.

8. The cell culture substrate of claim 1, wherein the peptide is GRGDY or GYIGSRY peptide.

9. The cell culture substrate of claim 1 wherein the peptide is attached to the substrate at a surface concentration of between about 0.5 picomoles/cm$^2$ to about 50 picomoles/cm$^2$.

10. The cell culture substrate of claim 1, wherein the peptide is attached to the substrate at a surface concentration of between about 0.5 picomoles/cm$^2$ to about 20 picomoles/cm$^2$.

11. The cell culture substrate of claim 1, wherein the peptide is attached to the substrate at a surface concentration of about 12 picomoles/cm$^2$.

12. The cell culture substrate of claim 1, wherein the substrate comprises a material selected from the group consisting of:
a ceramic;
a polymer; and
a metal.

13. The cell culture substrate of claim 12 wherein the metal is titanium.

14. The cell culture substrate of claim 1, wherein the substrate comprises:
a polymer; or
a ceramic.

15. The cell culture substrate of claim 1 or 5 wherein the substrate comprises a ceramic material.

16. The cell culture substrate of claim 15, wherein the ceramic is glass.

17. The cell culture substrate of claim 16, wherein the glass comprises glycerol propylsilane-bonded glass.

18. The cell culture substrate of claim 16, wherein the polymer is poly(hydroxyethyl methacrylate).

19. The cell culture substrate of claim 1, wherein the substrate comprises a polymer selected from the group consisting of:
a plastic;
a poly (hydroxyethyl methylacrylate);
a poly (ethylene terephthalate);
a poly (tetrafluoroethylene);
a fluorinated ethylene; and
a poly (dimethyl siloxane).

20. The cell culture substrate of claim 19, wherein the polymer is poly(ethylene terephthalate).

21. The cell culture substrate of claim 20, wherein the peptide is GRGD or GYIGSR.

22. The cell culture substrate of claim 1 wherein the substrate is essentially free of peptide throughout the substrate bulk.

23. The cell culture substrate of claim 22, wherein the peptide is within 10 nanometers of the substrate surface.

24. A cell culture substrate capable of supporting fibroblast focal adhesion formation and spreading comprising a surface derivatized with a peptide consisting essentially of GYIGSR, wherein said peptide is covalently linked by the terminal glycine to the surface.

25. A cell culture substrate capable of supporting cell focal adhesion formation and cell spreading comprising a surface derivatized with a peptide selected from the group consisting of GRGD, GRGDF, GRDGY, GYIGSR and GYIGSRY, and wherein the terminal glycine of said peptide is covalently linked to surface hydroxyl groups of the surface.

* * * * *

UNITED STATES PATENT AND TRADEMARK OFFICE
CERTIFICATE OF CORRECTION

PATENT NO. : 5,278,063
DATED : January 11, 1994
INVENTOR(S) : Hubbell et al

It is certified that error appears in the above-indentified patent and that said Letters Patent is hereby corrected as shown below:

On the title page, Item [54], and Col. 1, line 1, delete "OF" and insert —TO—.

Column 29, claim 2, line 22, delete "to" and insert —or—.
Column 29, claim 8, line 39, delete the second occurrence of "peptide".

Signed and Sealed this

Thirteenth Day of September, 1994

Attest:

BRUCE LEHMAN

Attesting Officer

Commissioner of Patents and Trademarks